(12) United States Patent

O'Dea

(10) Patent No.: US 12,589,212 B2

(45) Date of Patent: Mar. 31, 2026

(54) LEAK DETECTING APPARATUS AND A METHOD FOR DETECTING A LEAK IN A HOLLOW ORGAN OR LUMEN IN A HUMAN OR ANIMAL BODY

(71) Applicant: PALLIARE LIMITED, Galway (IE)

(72) Inventor: John O'Dea, Galway (IE)

(73) Assignee: Palliare Limited, Galway (IE)

( * ) Notice: Subject to any disclaimer, the term of this patent is extended or adjusted under 35 U.S.C. 154(b) by 901 days.

(21) Appl. No.: 17/262,672

(22) PCT Filed: Jul. 25, 2019

(86) PCT No.: PCT/IE2019/000008

§ 371 (c)(1),
(2) Date: Jan. 22, 2021

(87) PCT Pub. No.: WO2020/021520

PCT Pub. Date: Jan. 30, 2020

(65) Prior Publication Data

US 2021/0308390 A1      Oct. 7, 2021

(30) Foreign Application Priority Data

Jul. 25, 2018    (IE) .................................... 2018/0222

(51) Int. Cl.
A61M 13/00          (2006.01)

(52) U.S. Cl.
CPC ....... A61M 13/003 (2013.01); A61M 2205/15 (2013.01); A61M 2205/3334 (2013.01); A61M 2205/3344 (2013.01); A61M 2205/50 (2013.01)

(58) Field of Classification Search
CPC .. A61M 13/00; A61M 13/003; A61M 13/006; A61M 2205/15;

(Continued)

(56) References Cited

U.S. PATENT DOCUMENTS

2007/0123781 A1 *  5/2007  Callahan ................  A61B 5/036
                                                                    600/483
2007/0163604 A1 *  7/2007  Mikkaichi ..............  A61B 90/06
                                                                    128/898

(Continued)

OTHER PUBLICATIONS

European Patent Office; International Search Report and Written Opinion; PCT/IE2019/000008; Jul. 25, 2019.

*Primary Examiner* — Kami A Bosworth
*Assistant Examiner* — Avery Smale
(74) *Attorney, Agent, or Firm* — Sughrue Mion, PLLC

(57) ABSTRACT

A leak detecting apparatus (1) for detecting a leak and determining the size of the leak in a suture repaired site (5) of a hollow organ (3), for example, a stomach, in a cavity (7), for example, the peritoneal cavity of a subject comprises a first insufflator (12) for insufflating the hollow organ (3) with a first gas, and a second insufflator (14) for insufflating the cavity (7) with a second gas. A gas detector (18) is provided for detecting the concentration of the first gas in gases exhausted from the cavity (7) through a communicating conduit (35). A flow meter (25) monitors the flow rate of the first gas to the hollow organ (3). First and second pressure sensors (15) and (16) monitor the static pressure of the first and second gases in the hollow organ (3) and the cavity (7), respectively. The apparatus (1) is operable in a first mode and a second mode. In both the first and second modes of operation a microprocessor (50) controls the second insufflator (14) for maintaining the pressure in the cavity (7) at a relatively low predefined pressure, and the first insufflator (12) for maintaining a constant predefined pressure differential between the pressures in the hollow organ (3) and the cavity (7) of approximately 7 mmHg. In the first mode the microprocessor (50) determines the size of the leak as a function of the pressure differential and the concentration of the first gas in the exhaust gases. In the (Continued)

Figure 1:
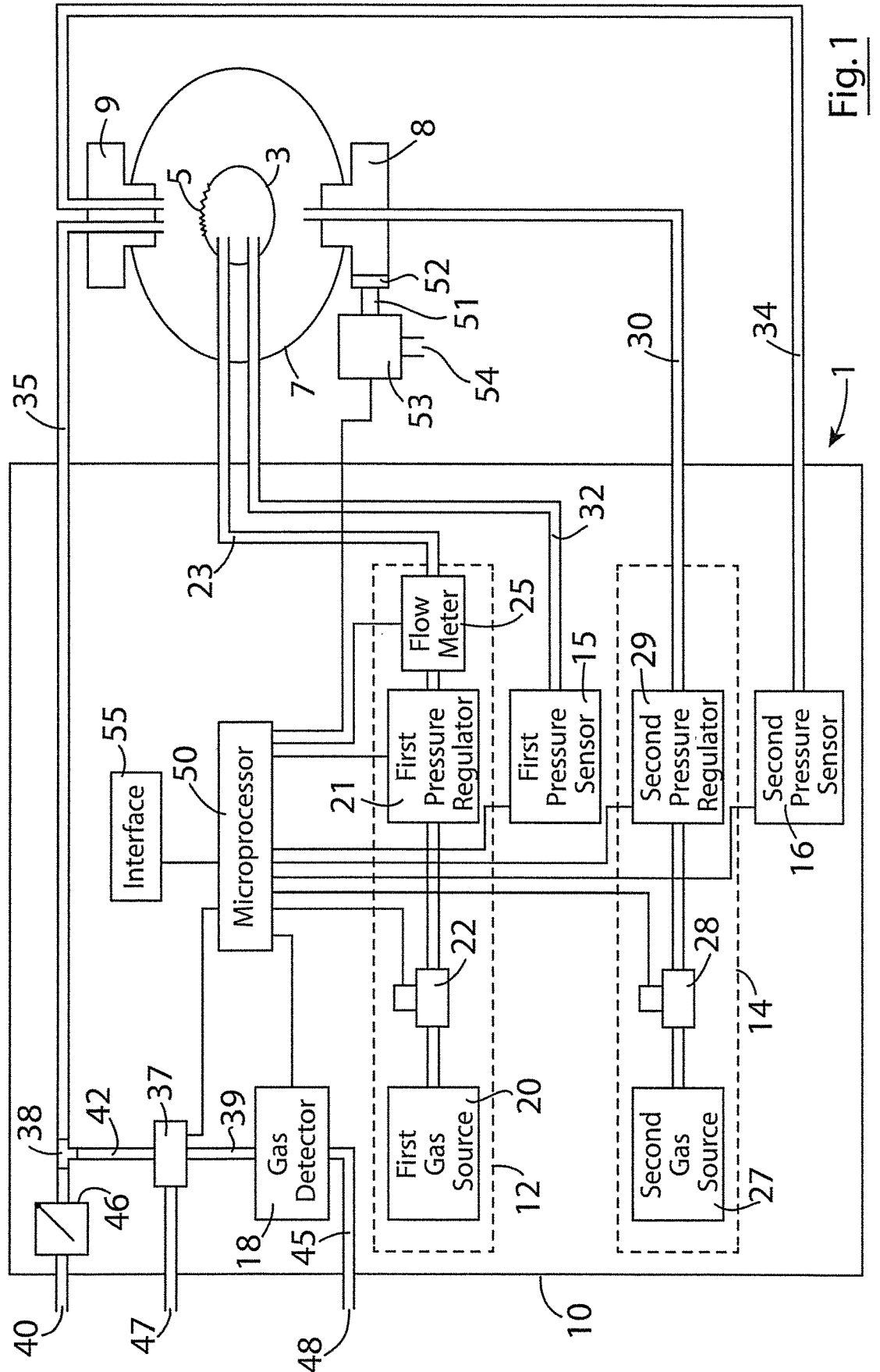

second mode of operation the microprocessor (50) deter-mines the size of the leak as a function of the pressure differential and the flow rate of the first gas to the hollow organ (3) with the hollow organ (3) sealed apart from the sutured site (5).

32 Claims, 4 Drawing Sheets

(58) Field of Classification Search
 CPC .. A61M 2205/3334; A61M 2205/3344; A61M
 2205/50; A61M 2005/006; A61B
 2505/05; A61B 5/4255
 See application file for complete search history.

(56) References Cited

U.S. PATENT DOCUMENTS

| | | | |
|---|---|---|---|
| 2013/0096399 A1 | 4/2013 | Scalici et al. | |
| 2014/0020043 A1 | 1/2014 | Yager et al. | |
| 2014/0200437 A1 | 7/2014 | Yager et al. | |
| 2015/0027249 A1 | 1/2015 | Sessions | |
| 2015/0272499 A1* | 10/2015 | Shlomovitz | A61B 5/14503 |
| | | | 600/560 |
| 2016/0331946 A1* | 11/2016 | Grziwa | A61M 27/00 |
| 2018/0280634 A1* | 10/2018 | O'Dea | A61M 13/003 |

* cited by examiner

LEAK DETECTING APPARATUS AND A METHOD FOR DETECTING A LEAK IN A HOLLOW ORGAN OR LUMEN IN A HUMAN OR ANIMAL BODY

CROSS-REFERENCE TO RELATED APPLICATIONS

This application is a United States national phase application under 35 U.S.C. § 371 of International Patent Application No. PCT/IE2019/000008, filed Jul. 25, 2019, which claims benefit of Irish Patent Application No. S2018/0222, filed Jul. 25, 2018, both of which are incorporated herein by reference in their entirety. The International Application published as International Publication No. WO 2020/021520 on Jan. 30, 2020.

The present invention relates to a leak detecting apparatus for detecting a leak in a hollow organ or lumen located in a cavity in a human or animal body, and the invention also relates to a method for detecting a leak in a hollow organ or lumen located in a cavity in a human or animal body.

In the field of general surgery on a human or animal subject, hollow organs and lumens, as well as other hollow tubular and other hollow structures, hereinafter referred to generally as hollow structures, are commonly repaired. Such surgery on such hollow structures frequently require stitching or stapling in order to close a portion of the wall of the structure. Another common procedure involves the joining of two portions of a lumen, or other hollow structure, after a cancerous portion of the lumen or structure has been excised ("anastomosis"). One recent study has found an over 8% leak rate for anastomotic leaks in oesophageal cancer surgery.

On completion of such surgical procedures, an important follow-on step involves a leak test to determine that the organ or other hollow structure is sealed at the repair site. This is essential in order to avoid any contents of the organ or other hollow structure passing from the hollow structure into the cavity in which the organ or hollow structure is located in the body of the subject. Any significant leakage from such a hollow structure into the cavity in which the hollow structure is located would in general lead to infection of the cavity.

One commonly used method for leak testing such as a repair to a hollow structure includes injecting a coloured die into the hollow structure, and under direct visualization observing if any of the die passes from the hollow structure into the cavity in which the hollow structure is located. Another commonly used method for testing for a leak in such a repair to a hollow structure requires instilling sterile liquid into the cavity in which the hollow structure is located and then injecting a gas into the hollow structure, and under direct visualization observing if bubbles resulting from gas leaking from the hollow structure form in the sterile liquid. If a leak from the hollow structure is observed in the closure or anastomosis, it is repaired, and retesting must then be performed.

The coloured die test method suffers from a serious disadvantage due to the fact that retesting of the repaired site cannot be accurately carried out, since colour die from the previous test remains in the cavity. The gas injection method suffers from two serious disadvantages. Firstly, the gas injection method is unsuitable in procedures where the hollow structure is located in a relatively large cavity. Secondly, in the event of a relatively small leak from the repaired site, a surgeon using the gas injection method may fail to observe small bubbles, since the successful observance of such bubbles largely depends on the line of sight to the repaired site, and the size of the defective part of the repair site.

A method for detecting a leak from a repaired site in a hollow structure has recently been developed, and is disclosed in U.S. Published Patent Application Specification No. 2015/0272499 of Shlomovitz. This test method requires the injection of a test gas into the hollow structure which has been repaired. The test gas ideally should be a gas which does not occur naturally in the human or animal body, or if it does, occurs in almost negligible quantities. A gas detector for detecting the test gas is provided for monitoring for the presence of the test gas either in the cavity or externally of the cavity in exhaust gases exhausted from the cavity, such as an insufflation gas which is being exhausted from the cavity. On detecting the test gas either in the cavity or in gases being exhausted from the cavity, the presence of a leak from the repaired site is confirmed. An advantage of this test method is that it is also suitable for retesting after the defective site has been repaired, due to the fact that the cavity can be readily easily purged of the test gas on completion of the test. This is particularly so in the case of laparoscopic procedures and micro-surgery, where the procedure is being carried out in an insufflated cavity. By increasing the flow of insufflating gas through the cavity in which the hollow structure is located, the test gas from a previous test can be readily and quickly purged from the cavity.

However, while the test method disclosed in U.S. Published Patent Application Specification No. 2015/0272499 of Shlomovitz is suitable for detecting a leak from a hollow structure into a cavity in which the hollow structure is located, it is unsuitable for determining the size of the leak from the hollow structure into the cavity. It is important for a surgeon to know the size of the leak in order to determine if further repair of the leaking site is required. For example, if the leak from the site is relatively small, a decision may be made to take no further action, since the leaking area of the site would automatically seal itself due to the body's natural ability to heal itself. While on the other hand a larger leak would require further surgical intervention.

U.S. Published Patent Application Specification No. 2013/0096399 of Scalici discloses a method and apparatus for detecting a perforation of the bowel of a human or animal subject resulting from a surgical procedure. The method of Scalici requires drawing a sample of gas from the abdominal or pelvic cavity and analysing the sample of gas for one or more of a gas occurring in the bowel, such as methane, hydrogen, carbon dioxide, sulphide and other fermentable gases that are released by bacterial metabolism, such as, nitrogen and sulphide acetate. These gases exist in different concentrations in the small and large bowel, and are normally not present in the abdominal or pelvic cavities. Thus, detection of any of these gases in the sample of gas drawn from the abdominal or pelvic cavity is an indication of a leak from the bowel. The method of Scalici requires relatively sensitive gas detecting devices, and additionally, while it may give an indication of a leak from the bowel, it is incapable of giving an indication of the size of the leak.

U.S. Published Patent Application Specification No. 2014/0200437 of Yager discloses a method for detecting a colorectal leak into the abdominal or pelvic cavity. The method of Yager requires placing a patient in a magnetic resonance imaging machine or in a nuclear magnetic resonance imaging machine and delivering into the rectum or colon of the patient a gas mixture which includes hyperpolarized 3-He and 4-He. The hyperpolarized 3-He and 4-He gas mixture is delivered through a patient tube which is inserted into the patient through the anus. Images of the abdominal or pelvic cavity of the patient are captured by the magnetic resonance imaging machine or the nuclear magnetic resonance imaging machine, and the detection of the hyperpolarized 3-He and 4-He gas mixture in the abdominal or pelvic cavity is an indication of colorectal leakage. While Yager may give an indication of colorectal leakage, it is incapable of giving an indication of the size of the leakage.

U.S. Published Patent Application Specification No. 2007/0163604 of Mikkaichi discloses a method for detecting a leak from a hollow organ, for example, the stomach of a subject into the abdominal cavity through a sutured or otherwise closed opening in the stomach which typically, would have been formed as a result of a surgical procedure. The abdominal cavity is insufflated with a carbon dioxide gas, and the stomach is filled or partly filled with water such that the water covers the sutured opening. A vision system located in the stomach is used to detect bubbles forming in the water in the stomach as a result of leakage of the carbon dioxide gas from the abdominal cavity into the stomach through the sutured site. In an alternative embodiment of the method of Mikkaichi the stomach is evacuated and the abdominal cavity is insufflated with air to a known pressure, at which stage insufflating of the abdominal cavity ceases. The pressure in the abdominal cavity is monitored, and a fall in the pressure in the abdominal cavity is indicative of a leak from the abdominal cavity into the stomach through the sutured site. However, while both methods of Mikkaichi give an indication of a leak through the sutured site in the stomach, they are incapable of giving an indication of the size of the leak.

There is therefore a need for a leak detecting apparatus for detecting a leak in a hollow structure located in a cavity in a human or animal body which addresses the problem of prior apparatus, and which provides an indication of the size of the leak. There is also a need for a method for detecting a leak in a hollow structure located in a cavity in a human or animal body which also addresses the problem of prior art methods, and which provides an indication of the size of the leak.

The present invention is directed towards providing such a leak detecting apparatus and a method.

According to the invention there is provided a leak detecting apparatus for detecting a leak in a hollow structure located in a cavity in a human or animal body, the leak detection apparatus comprising:

a first insufflator configured to deliver a first gas into one of the hollow structure and the cavity, a first pressure sensing means configured to produce a signal indicative of the pressure in the hollow structure, a second pressure sensing means configured to produce a signal indicative of the pressure in the cavity, a control means configured for controlling the pressure in one of the hollow structure and the cavity for maintaining a substantially constant pressure differential between the pressure in the hollow structure and the pressure in the cavity, one of a gas detecting means configured to produce a signal indicative of the presence of the first gas in the one of the hollow structure and the cavity into which the first gas is not delivered, and a gas flow sensing means configured to produce a signal indicative of the rate of flow of the first gas delivered to the one of the hollow structure and the cavity, and a computing means configured to compute the size of the leak as a function of the pressure differential between the pressures in the hollow structure and the cavity, and one of the detected first gas in the one of the hollow structure and the cavity into which the first gas is not delivered, and the rate of flow of the first gas to the one of the hollow structure and the cavity.

Preferably, the control means is configured for controlling the pressure in the one of the hollow structure and the cavity, so that the pressure in the one of the hollow structure and the cavity into which the first gas is delivered, is at a higher pressure than the pressure in the other one of the hollow structure and the cavity.

In one embodiment of the invention the control means is configured for controlling the pressure in the one of the hollow structure and the cavity, into which the first gas is delivered, for maintaining the pressure differential between the pressure in the hollow structure and the pressure in the cavity substantially constant at a predefined pressure differential value.

Preferably, the predefined pressure differential value lies in the range of 3 mmHg to 12 mmHg. Advantageously, the predefined pressure differential value lies in the range of 5 mmHg to 10 mmHg.

Ideally, the predefined pressure differential value is approximately 7 mmHg. Preferably, the predefined pressure differential value is selectable.

In another embodiment of the invention the control means is configured to control the pressure in the one of the hollow structure and the cavity relative to the pressure in the other one of the hollow structure and the cavity.

In another embodiment of the invention the control means is configured to control the pressure in the one of the hollow structure and the cavity, into which the first gas is delivered, relative to the pressure in the other one of the hollow structure and the cavity.

In a further embodiment of the invention the control means is responsive to the signals produced by the first and second pressure sensing means indicative of the pressures in the hollow structure and the cavity, respectively, for controlling the pressure in the one of the hollow structure and the cavity.

In one embodiment of the invention the first insufflator is configured to operate under the control of the control means.

Preferably, the first insufflator is configured to deliver the first gas to the one of the hollow structure and the cavity in response to signals from the control means.

In another embodiment of the invention the control means is configured to read signals produced by the first and second pressure sensing means.

In one embodiment of the invention the computing means is configured to compute the size of the leak from the signals produced by the first and second pressure sensing means.

In another embodiment of the invention the gas detecting means is configured to monitor gases in or exhausted from the one of the hollow structure and the cavity, into which the first gas is not delivered, for producing the signal indicative of the presence of the first gas in that one of the hollow structure and the cavity.

Preferably, the gas detecting means is configured to sample the gases in or exhausted from the one of the hollow structure and the cavity, into which the first gas is not delivered, for producing the signal indicative of the presence of the first gas in that one of the hollow structure and the cavity.

Preferably, the control means is configured to read signals produced by the gas detecting means.

In one embodiment of the invention the control means is configured to read signals produced by the gas detecting means at predefined sampling time intervals.

Preferably, each predefined sampling time interval lies in the range of 0.01 seconds to 2 seconds.

Advantageously, each predefined sampling time interval lies in the range of 0.1 seconds to 1 second.

Ideally, each predefined sampling time interval lies in the range of 0.5 seconds to 1 second. Preferably, the duration of the predefined sampling time intervals is selectable.

In one embodiment of the invention the gas detecting means is configured to produce the signal indicative of the presence of the first gas in the one of the hollow structure and the cavity, into which the first gas is not delivered, as a signal indicative of the concentration of the first gas in the gases in or exhausted from that one of the hollow structure and the cavity.

In another embodiment of the invention the computing means is configured to compute the size of the leak as a function of the concentration of the first gas in the gases in or exhausted from the one of the hollow structure and the cavity, into which the first gas is not delivered, detected by the gas detecting means.

In another embodiment of the invention the computing means is configured to compute the size of the leak as a function of the rate of change in the concentration of the first gas in the gases in or exhausted from the one of the hollow structure and the cavity, into which the first gas is not delivered.

In a further embodiment of the invention the computing means is configured to compute the size of the leak as a function of the concentration of the first gas in the gases in or exhausted from the one of the hollow structure and the cavity, into which the first gas is not delivered, during a predefined time period.

In another embodiment of the invention the computing means is configured to compute the size of the leak as a function of the concentration of the first gas in the gases in or exhausted from the one of the hollow structure and the cavity, into which the first gas is not delivered, at the end of the predefined time period.

In a further embodiment of the invention the computing means is configured to compute the size of the leak as a function of the integral of the concentration of the first gas in the gases in or exhausted from the one of the hollow structure and the cavity, into which the first gas is not delivered, with respect to time during the predefined time period or a part thereof.

In another embodiment of the invention the predefined time period commences on commencement of the delivery of the first gas to the one of the hollow structure and the cavity.

Preferably, the predefined time period lies in the range of 10 seconds to 120 seconds. Advantageously, the predefined time period lies in the range of 30 seconds to 100 seconds.

Ideally, the predefined time period lies in the range of 40 seconds to 60 seconds. Preferably, the duration of the predefined time period is selectable.

In another embodiment of the invention the control means is configured to read signals produced by the gas flow sensing means.

Preferably, the computing means is configured to compute the size of the leak from the signals produced by the gas flow sensing means.

In one embodiment of the invention the first insufflator comprises a first pressure control means for controlling the pressure at which the first gas is delivered to the one of the hollow structure and the cavity. Preferably, the first pressure control means is responsive to signals from the control means for controlling the pressure at which the first gas is delivered to the one of the hollow structure and the cavity.

In another embodiment of the invention the gas flow sensing means is configured for monitoring the rate of flow of the first gas delivered from the first pressure control means.

In a further embodiment of the invention a first delivery conduit is provided for delivering the first gas from the first insufflator to the one of the hollow structure and the cavity.

In another embodiment of the invention the one of the first pressure sensing means and the second pressure sensing means is configured to monitor the pressure in the corresponding one of the hollow structure and the cavity through the first delivery conduit.

In an alternative embodiment of the invention the first pressure sensing means is configured to monitor the pressure in the hollow structure through a first static pressure conduit communicating the first pressure sensing means with the hollow structure.

In one embodiment of the invention the first pressure sensing means is located adjacent the first insufflator. In an alternative embodiment of the invention the first pressure sensing means is configured for locating adjacent the hollow structure.

In another embodiment of the invention the second pressure sensing means is configured to monitor the pressure in the cavity through a second static pressure conduit communicating the second pressure sensing means with the cavity.

In one embodiment of the invention the second pressure sensing means is located adjacent the first insufflator. In an alternative embodiment of the invention the second pressure sensing means is configured for locating adjacent the cavity.

In one embodiment of the invention the gas detecting means is configured to sample the gases in or exhausted from the one of the hollow structure and the cavity, into which the first gas is not delivered, by side-stream sampling.

In another embodiment of the invention a communicating conduit communicates the gas detecting means with the one of the hollow structure and the cavity, into which the first gas is not delivered, for delivering gases exhausted from that one of the hollow structure and the cavity to the gas detecting means.

In another embodiment of the invention the communicating conduit terminates in a first exhaust port configured to communicate with room air.

Preferably, the gas detecting means communicates with the communicating conduit upstream of the first exhaust port.

Advantageously, the communicating conduit communicates with the first exhaust port through a one-way valve, the one-way valve being configured to permit flow from the communicating conduit through the first exhaust port. Preferably, the gas detecting means communicates with the communicating conduit upstream of the on-way valve.

In another embodiment of the invention the gas detecting means communicates with the communicating conduit through a first valving means.

Preferably, the first valving means is operable selectively and alternately in a first state communicating the gas detecting means with the communicating conduit and in a second state communicating the gas detecting means with an inlet port configured to communicate with room air. Advantageously, the first valving means is operable under the control of the control means.

In another embodiment of the invention the communicating conduit is configured to communicate with the cavity through a trocar.

In a further embodiment of the invention a second valving means selectively communicates the cavity with a second exhaust port configured to communicate with room air. Preferably, the second valving means is operable under the control of the control means.

Preferably, the first insufflator comprises a pressurised source of the first gas.

In one embodiment of the invention a second insufflator is provided, the second insufflator being configured to insufflate the one of the hollow structure and the cavity, into which the first gas is not delivered, with a second gas. In another embodiment of the invention the second insufflator is configured to operate under the control of the control means for controlling the pressure in the one of the hollow structure and the cavity, into which the second gas is delivered.

Preferably, the second insufflator is operated under the control of the control means in response to signals produced by one or both of the first and second pressure sensing means.

In another embodiment of the invention the second insufflator is operated under the control of the control means for maintaining the pressure in the one of the hollow structure and the cavity, into which the second gas is delivered, at a predefined pressure value.

Preferably, the predefined pressure value lies in the range of 5 mmHg to 10 mmHg. Advantageously, the predefined pressure value lies in the range of 5 mmHg to 8 mmHg. Ideally, the predefined pressure value is approximately 5 mmHg. Preferably, the predefined pressure value is selectable.

In one embodiment of the invention the second insufflator comprises a second pressure control means for controlling the pressure at which the second gas is delivered to the one of the hollow structure and the cavity.

In another embodiment of the invention the second pressure control means is operated under the control of the control means in response to signals produced by the one of the first pressure sensing means and the second pressure sensing means for controlling the pressure at which the second gas is delivered to the one of the hollow structure and the cavity. In a further embodiment of the invention a second delivery conduit communicates the second insufflator with the one of the hollow structure and the cavity for delivering the second gas from the second insufflator to the one of the hollow structure and the cavity.

In one embodiment of the invention the one of the first pressure sensing means and the second pressure sensing means is configured to monitor the pressure in the corresponding one of the hollow structure and the cavity through the second delivery conduit.

In another embodiment of the invention the second delivery conduit is configured for delivering the second gas to the cavity through a trocar.

In another embodiment of the invention the second insufflator comprises a pressurised source of the second gas.

In one embodiment of the invention the first gas may be the same as the second gas or different to the second gas. In another embodiment of the invention the first gas is different to the second gas. In an alternative embodiment of the invention the first gas is the same as the second gas.

In a further embodiment of the invention the second gas comprises carbon dioxide.

In one embodiment of the invention the second insufflator comprises a part of the leak detecting apparatus.

In an alternative embodiment of the invention the second insufflator is provided by an external insufflator separately from the leak detecting apparatus.

In a further embodiment of the invention the leak detecting apparatus is configured to operate in conjunction with the external insufflator.

In another embodiment of the invention the control means of the leak detecting apparatus is configured to control the operation of the external insufflator through a communicating means.

In another embodiment of the invention the control means of the leak detecting apparatus is configured to control the external insufflator through a wireless communicating means.

In a further embodiment of the invention the control means of the leak detecting apparatus is configured to control the external insufflator through a hardwired communicating means.

In one embodiment of the invention a diverting valve is provided, the diverting valve being selectively and alternately operable in a normal state for delivering the second gas from the external insufflator to the one of the hollow structure and the cavity, and in a diverting state for delivering the second gas from the external insufflator to a reservoir.

Preferably, the reservoir comprises a balloon.

In another embodiment of the invention the reservoir is configured for maintaining the pressure of the second gas delivered by the external insufflator at a pressure value corresponding to a normal operating pressure value at which the external insufflator is configured to operate.

In another embodiment of the invention the diverting valve is operated under the control of the control means of the leak detecting apparatus.

In a further embodiment of the invention the second insufflator is configured to deliver the second gas to the cavity.

In one embodiment of the invention the first insufflator is configured to deliver the first gas to the hollow structure.

In another embodiment of the invention the first gas comprises one of a gas not naturally occurring in the hollow organ or the cavity of the human or animal body, and a gas the amount of which occurring naturally in the hollow organ or the cavity of the human or animal body occurs in negligible amounts, and preferably, the first gas comprises a gas not occurring naturally in the human or animal body, or in negligible amounts only therein.

Preferably, the first gas comprises nitrous oxide ($N_2O$).

The invention also provides a leak detecting apparatus for detecting a leak from a hollow structure in a human or animal body to a cavity in the human or animal body, the leak detection apparatus comprising:

a first insufflator configured to deliver a first gas into the hollow structure, a first pressure sensing means configured to produce a signal indicative of the pressure in the hollow structure, a second pressure sensing means configured to produce a signal indicative of the pressure in the cavity, a control means configured for controlling the pressure in one of the hollow structure and the cavity for maintaining a substantially constant pressure differential between the pressure in the hollow structure and the pressure in the cavity, one of a gas detecting means configured to produce a signal indicative of the presence of the first gas in the cavity, and a gas flow sensing means configured to produce a signal indicative of the rate of flow of the first gas delivered to the hollow structure, and a computing means configured to compute the size of the leak as a function of the pressure differential between the pressures in the hollow structure and the cavity, and one of the detected first gas in the cavity, and the rate of flow of the first gas to the hollow structure.

In one embodiment of the invention the control means is configured for controlling the pressure in the one of the hollow structure and the cavity so that the pressure in the hollow structure is at a higher pressure than the pressure in the cavity.

In another embodiment of the invention the control means is configured for controlling the pressure in the one of the hollow structure and the cavity for maintaining the pressure differential between the pressure in the hollow structure and the pressure in the cavity substantially constant at a predefined pressure differential value.

In another embodiment of the invention the control means is configured to control the pressure in the one of the hollow structure and the cavity relative to the pressure in the other one of the hollow structure and the cavity.

Preferably, the control means is configured to control the pressure in the hollow structure relative to the pressure in the cavity.

In another embodiment of the invention the control means is responsive to the signals produced by the first and second pressure sensing means indicative of the pressures in the hollow structure and the cavity, respectively, for controlling the pressure in the one of the hollow structure and the cavity.

Preferably, the first insufflator is configured to deliver the first gas to the hollow structure in response to signals from the control means.

In one embodiment of the invention the computing means is configured to compute the size of the leak from the signals produced by the first and second pressure sensing means.

In another embodiment of the invention the gas detecting means is configured to monitor gases exhausted from the cavity for producing the signal indicative of the presence of the first gas in the cavity.

In another embodiment of the invention the gas detecting means is configured to sample the gases exhausted from the cavity for producing the signal indicative of the presence of the first gas in the cavity.

In one embodiment of the invention the gas detecting means is configured to produce the signal indicative of the presence of the first gas in the cavity as a signal indicative of the concentration of the first gas in the gases in or exhausted from the cavity.

In another embodiment of the invention the computing means is configured to compute the size of the leak as a function of the concentration of the first gas in the gases in or exhausted from the cavity detected by the gas detecting means.

In another embodiment of the invention the computing means is configured to compute the size of the leak as a function of the rate of change in the concentration of the first gas in the gases in or exhausted from the cavity.

In another embodiment of the invention the computing means is configured to compute the size of the leak as a function of the concentration of the first gas in the gases in or exhausted from the cavity during a predefined time period.

In another embodiment of the invention the computing means is configured to compute the size of the leak as a function of the concentration of the first gas in the gases in or exhausted from the cavity at the end of the predefined time period.

In another embodiment of the invention the computing means is configured to compute the size of the leak as a function of the integral of the concentration of the first gas in the gases in or exhausted from the cavity with respect to time during the predefined time period or a part thereof.

In a further embodiment of the invention the predefined time period commences on commencement of the delivery of the first gas to the hollow structure.

In one embodiment of the invention the first insufflator comprises a first pressure control means for controlling the pressure at which the first gas is delivered to the hollow structure.

In another embodiment of the invention the first pressure control means is responsive to signals from the control means for controlling the pressure at which the first gas is to be delivered to the hollow structure.

In one embodiment of the invention a first delivery conduit is provided for delivering the first gas from the first insufflator to the hollow structure.

In another embodiment of the invention the first pressure sensing means is configured to monitor the pressure in the hollow structure through the first delivery conduit. In an alternative embodiment of the invention the first pressure sensing means is configured to monitor the pressure in the hollow structure through a first static pressure conduit communicating the first pressure sensing means with the hollow structure.

In one embodiment of the invention the first pressure sensing means is configured for locating adjacent the first insufflator.

In another embodiment of the invention the first pressure sensing means is configured for locating adjacent the hollow structure.

In another embodiment of the invention the second pressure sensing means is configured to monitor the pressure in the cavity through a second static pressure conduit communicating the second pressure sensing means with the cavity.

In a further embodiment of the invention the second pressure sensing means is located adjacent the first insufflator.

In another embodiment of the invention the second pressure sensing means is configured for locating in the cavity.

In a further embodiment of the invention the gas detecting means is configured to sample the exhaust gases in or exhausted from the cavity by side-stream sampling.

In another embodiment of the invention a communicating conduit communicates the gas detecting means with the cavity for delivering gases exhausted from the cavity to the gas detecting means.

In one embodiment of the invention the communicating conduit is configured to communicate with the cavity through a trocar.

In another embodiment of the invention a second valving means selectively communicates the cavity with a second exhaust port configured to communicate with room air.

In one embodiment of the invention the first insufflator comprises a pressurised source of the first gas.

In another embodiment of the invention a second insufflator is provided, the second insufflator being configured to insufflate the cavity with a second gas.

In one embodiment of the invention the second insufflator is configured to operate under the control of the control means for controlling the pressure in the cavity.

In another embodiment of the invention the second insufflator is operated under the control of the control means in response to signals produced by one or both of the first and second pressure sensing means.

In a further embodiment of the invention the second insufflator is operated under the control of the control means for maintaining the pressure in the cavity at a predefined pressure value.

Preferably, the second insufflator comprises a second pressure control means for controlling the pressure at which the second gas is delivered to the cavity.

Advantageously, the second pressure control means is operated under the control of the control means in response to signals produced by the second pressure sensing means for controlling the pressure at which the second gas is delivered to the cavity.

In one embodiment of the invention a second delivery conduit communicates the second insufflator with the cavity for delivering the second gas from the second insufflator to the cavity.

In another embodiment of the invention the second pressure sensing means is configured to monitor the pressure in the cavity through the second delivery conduit.

In one embodiment of the invention a diverting valve is provided, the diverting valve being selectively and alternately operable in a normal state for delivering the second gas from the external insufflator to the cavity, and in a diverting state for delivering the second gas from the external insufflator to a reservoir.

Additionally, the invention provides a method for detecting a leak in a hollow structure located in a cavity in the human or animal body, the method comprising:

delivering a first gas into one of the hollow structure and the cavity, monitoring the pressure in the hollow structure, monitoring the pressure in the cavity, controlling the pressure in one of the hollow structure and the cavity for maintaining a substantially constant pressure differential between the pressure in the hollow structure and the pressure in the cavity, one of monitoring the gas in or from the one of the hollow structure and the cavity into which the first gas is not delivered for the presence of the first gas, and the rate of flow of the first gas delivered to the one of the hollow structure and the cavity, and computing the size of the leak as a function of the pressure differential between the pressures in the hollow structure and the cavity, and one of the detected gas in the one of the hollow structure and the cavity into which the first gas is not delivered, and the rate of flow of the first gas to the one of the hollow structure and the cavity.

In one embodiment of the invention the pressure in the one of the hollow structure and the cavity is controlled, so that the pressure in the one of the hollow structure and the cavity into which the first gas is delivered, is at a higher pressure than the pressure in the other one of the hollow structure and the cavity.

In another embodiment of the invention the pressure in the one of the hollow structure and the cavity, into which the first gas is delivered, is controlled for maintaining the pressure differential between the pressure in the hollow structure and the pressure in the cavity substantially constant at a predefined pressure differential value.

In one embodiment of the invention the pressure in the one of the hollow structure and the cavity is controlled relative to the pressure in the other one of the hollow structure and the cavity. Preferably, the pressure in the one of the hollow structure and the cavity, into which the first gas is delivered, is controlled relative to the pressure in the other one of the hollow structure and the cavity.

Advantageously, the pressure in the one of the hollow structure and the cavity is controlled in response to the pressures in the hollow structure and the cavity.

In one embodiment of the invention the gases in or exhausted from the one of the hollow structure and the cavity, into which the first gas is not delivered, are sampled for detecting the presence of the first gas in that one of the hollow structure and the cavity.

Preferably, the gases in or exhausted from the one of the hollow structure and the cavity, into which the first gas is not delivered, are sampled at predefined sampling time intervals for detecting the concentration of the first gas therein.

In one embodiment of the invention the size of the leak is computed as a function of the concentration of the first gas in the gases in or exhausted from the one of the hollow structure and the cavity, into which the first gas is not delivered.

In another embodiment of the invention the size of the leak is computed as a function of the rate of change in the concentration of the first gas in the gases in or exhausted from the one of the hollow structure and the cavity, into which the first gas is not delivered.

In another embodiment of the invention the size of the leak is computed as a function of the concentration of the first gas in the gases in or exhausted from the one of the hollow structure and the cavity, into which the first gas is not delivered, during a predefined time period.

In another embodiment of the invention the size of the leak is computed as a function of the concentration of the first gas in the gases in or exhausted from the one of the hollow structure and the cavity, into which the first gas is not delivered, at the end of the predefined time period.

In another embodiment of the invention the size of the leak is computed as a function of the integral of the concentration of the first gas in the gases in or exhausted from the one of the hollow structure and the cavity, into which the first gas is not delivered, with respect to time during the predefined time period or a part thereof.

In a further embodiment of the invention the predefined time period commences on commencement of the delivery of the first gas to the one of the hollow structure and the cavity.

In another embodiment of the invention a second gas is delivered into the one of the hollow structure and the cavity, into which the first gas is not delivered.

In another embodiment of the invention the pressure in the one of the hollow structure and the cavity, into which the second gas is delivered, is maintained at a predefined pressure value.

Further, the invention provides a method for detecting a leak from a hollow structure in a human or animal body to a cavity in the human or animal body, the method comprising:

delivering a first gas into the hollow structure,
monitoring the pressure in the hollow structure,
monitoring the pressure in the cavity,
controlling the pressure in one of the hollow structure and
    the cavity for maintaining a substantially constant
    pressure differential between the pressure in the hollow
    structure and the pressure in the cavity,
one of
    monitoring one of the gas in the cavity and gas
        exhausted from the cavity for the presence of the first
        gas, and
    the rate of flow of the first gas delivered to the hollow
        structure, and computing the size of the leak as a
        function of the pressure differential between the
        pressures in the hollow structure and the cavity, and
    one of
    the detected gas in the cavity, and
    the rate of flow of the first gas to the hollow structure.

In one embodiment of the invention the pressure in one of the hollow structure and the cavity is controlled so that the pressure in the hollow structure is higher than the pressure in the cavity.

In another embodiment of the invention the pressure in the one of the hollow structure and the cavity is controlled for maintaining the pressure differential between the pressure in the hollow structure and the pressure in the cavity substantially constant at a predefined pressure differential value.

In one embodiment of the invention the pressure in one of the hollow structure and the cavity is controlled relative to the pressure in the other one of the hollow structure and cavity.

Preferably, the pressure in the hollow structure is controlled.

Advantageously, the pressure in the one of the hollow structure and the cavity is controlled in response to the pressures in the hollow structure and the cavity.

Preferably, the size of the leak is computed as a function of the pressure differential between the pressures in the hollow structure and the cavity.

Advantageously, the gases in or exhausted from the cavity are monitored for the presence of the first gas.

Preferably, the gases in or exhausted from the cavity are sampled for detecting the presence of the first gas.

Advantageously, the gases in or exhausted from the cavity, are sampled at predefined sampling time intervals for detecting the concentration of the first gas therein.

In one embodiment of the invention the size of the leak is computed as a function of the concentration of the first gas detected in the gases in or exhausted from the cavity.

In another embodiment of the invention the size of the leak is computed as a function of the rate of change in the concentration of the first gas detected in the gases in or exhausted from the cavity during the predefined time period.

In another embodiment of the invention the size of the leak is computed as a function of the concentration of the first gas detected in the gases in or exhausted from the cavity during a predefined time period.

In another embodiment of the invention the size of the leak is computed as a function of concentration of the first gas detected at the end of the predefined time period.

In another embodiment of the invention the size of the leak is computed as a function of the integral of the concentration of the first gas detected in or exhausted from the cavity with respect to time during the predefined time period or a part thereof.

In a further embodiment of the invention the predefined time period commences at the time the first gas is delivered by the first insufflator to the hollow structure.

Preferably, the first gas is delivered to the hollow structure by a first insufflator.

Advantageously, a second gas is delivered to the cavity.

Preferably, the cavity is insufflated with the second gas.

Advantageously, the cavity is insufflated with the second gas by a second insufflator.

Preferably, the pressure in the cavity is maintained at a predefined pressure value.

The advantages of the invention are many. A particularly important advantage of the invention is that as well as detecting the presence of a leak from a repaired hollow structure or organ in a cavity, the apparatus according to the invention also determines the size of the leak. This is a particularly important advantage, in that in some cases, where a leak is relatively small, further repair may not be required in order to fully eliminate the leak, since in relatively small leaks, the natural healing ability of the body would be sufficient to seal off the leak, and therefore, unnecessary additional surgery is eliminated.

Another important advantage of the invention is achieved when the apparatus is configured to detect a leak and to determine the size of the leak by delivering a first gas into the one of the hollow structure and the cavity, when the first gas comprises either a gas not naturally occurring in the hollow structure or the cavity of the human or animal body, or a gas, the amount of which occurring naturally in the hollow structure and the cavity of the human or animal body, occurs in negligible amounts. The advantage of the apparatus when the first gas comprises such a gas is that the apparatus is suitable for determining the size of a leak through a sutured site in a hollow structure in a human or animal body, even when the hollow structure cannot be sealed, for example, in a lumen, which may be open at one or both ends. This is due to the fact that other leaks in the hollow structure have no effect on the concentration of the first gas detected in the gases in or exhausted from the one of the hollow structure and the cavity resulting from the leak through the sutured site, provided that any of the other leaks in the hollow structure do not communicate with the cavity, and provided also that the pressure differential between the pressures in the hollow structure and the cavity is maintained constant during the test.

The advantage of operating the apparatus with such a first gas, which does not occur naturally or occurs in negligible amounts only in the hollow structure or the cavity, is particularly achieved when the first gas is delivered into the hollow structure and detected in the cavity, in that firstly, even when the hollow structure cannot be sealed, the size of the leak can still be determined, and secondly, the apparatus can be readily, easily and conveniently attached to a subject, and particularly to a subject, who is undergoing a procedure through laparoscopic surgery. The concentration of the first gas in the gases exhausted from the cavity will be the same irrespective of whether or not the hollow structure is sealed apart from the sutured site.

A further advantage of the invention is that the apparatus according to the invention may be provided to include a second insufflator, or may be provided without a second insufflator, and if provided without a second insufflator, is configurable to operate in conjunction with an external insufflator.

A further advantage of the leak detecting apparatus is that as well as being suitable for detecting a leak and the size of a leak from a hollow structure to a cavity, in which the hollow structure is located, resulting from a repaired site in the hollow structure, for example, a sutured repaired site, the apparatus is also suitable for detecting a leak, and the size of the leak from a hollow structure to a cavity, in which the hollow structure is located, where the leak is through a perforation of the hollow structure which may have resulted from disease or other causes.

The advantages of the method according to the invention for detecting a leak in a hollow structure located in a cavity in a human or animal body are similar to those of the apparatus according to the invention.

Figure 2:
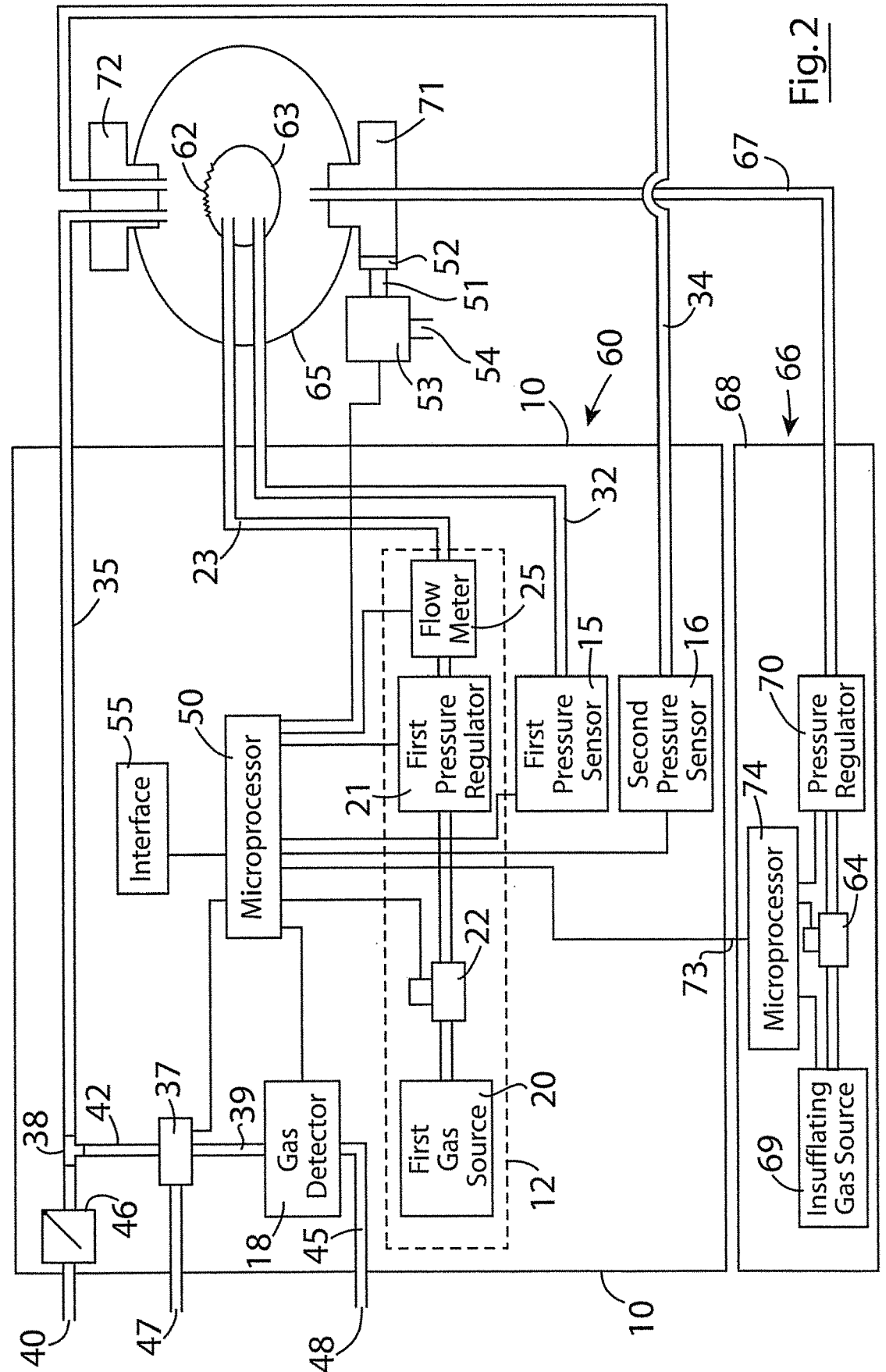
Figure 3:
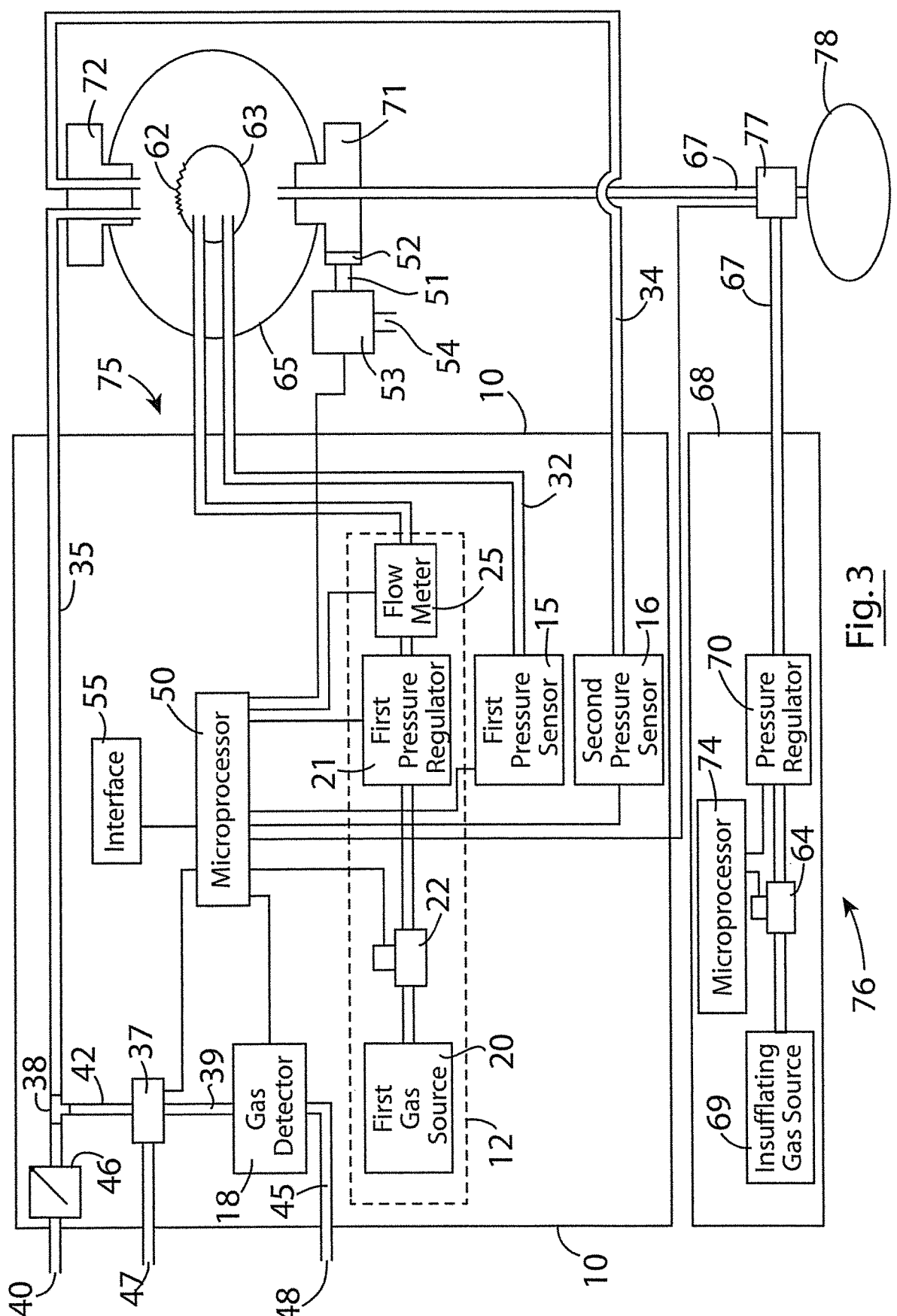
Figure 4:
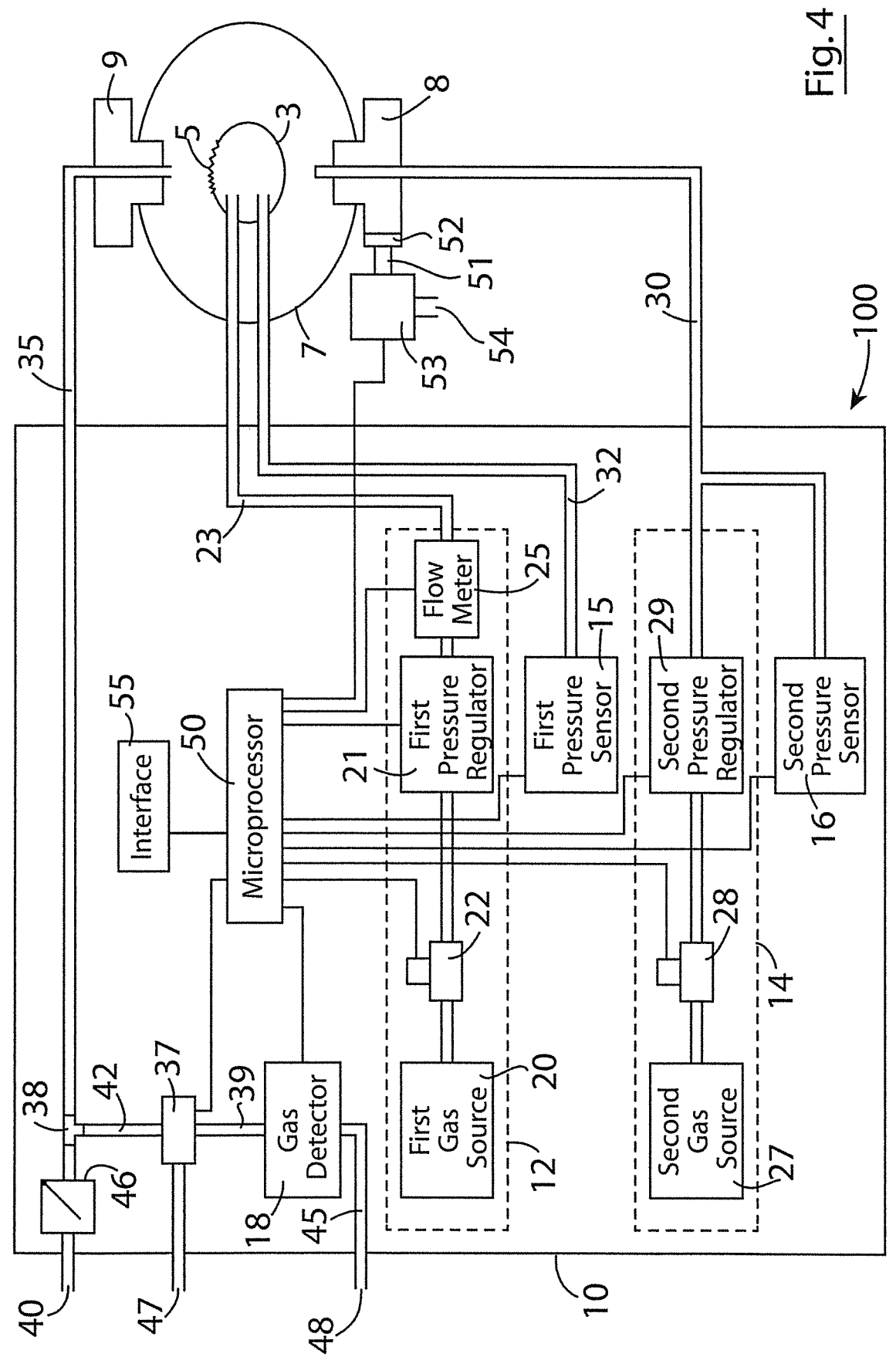

The invention will be more clearly understood from the following description of some preferred embodiments thereof which are given by way of example only with reference to the accompanying drawings, in which:

FIG. 1 is a block representation of leak detecting apparatus according to the invention for detecting a leak in a hollow structure, for example, a hollow organ in a cavity in a human or animal body, FIG. 2 is a block representation of a leak detecting apparatus according to another embodiment of the invention for detecting a leak in a hollow structure, for example, a hollow organ in a cavity in a human or animal body, FIG. 3 is a block representation of a leak detecting apparatus according to another embodiment of the invention for detecting a leak in a hollow structure, for example, a hollow organ in a cavity in a human or animal body, and FIG. 4 is a block representation of a leak detecting apparatus according to another embodiment of the invention for detecting a leak in a hollow structure, for example, a hollow organ in a cavity in a human or animal body.

Referring to the drawings, and initially to FIG. 1 thereof, there is illustrated a leak detecting apparatus according to the invention indicated generally by the reference numeral 1 for detecting a leak and determining the size of the leak in a hollow structure, in this embodiment of the invention, a hollow organ 3, for example, a stomach through a perforated or repaired site, such as for example, a sutured site 5 in the hollow organ 3 into a cavity 7, for example, the peritoneal cavity in the body (not shown) of a human or animal subject. The apparatus 1 is operable in two modes of operation as will be described below, and is particularly suitable for detecting a leak through such a perforated, sutured or otherwise repaired site 5 in a hollow organ 3 into a cavity 7 during a laparoscopic procedure during which the site 5 is sutured, and for determining the size of the leak. One or more trocars are provided through the body of the subject for providing access into the cavity 7 for surgical instruments, as well as for accommodating insufflating gas into the cavity for insufflating thereof, as will be described in more detail below. In this case two trocars are provided, namely, a first trocar 8 and a second trocar 9. Although it is envisaged that in some cases more than two trocars may be provided.

The apparatus 1 comprises a housing 10 within which the components of the apparatus 1 are housed. The apparatus 1 comprises a first insufflator 12 located in the housing 10 for insufflating one of the hollow organ 3 and the cavity 7 with a first gas. In this embodiment of the invention the first insufflator 12 is configured for insufflating the hollow organ 3 with the first gas. A second insufflator 14 is also located in the housing 10 for insufflating the other one of the hollow organ 3 and the cavity 7 with a second gas. In this embodiment of the invention the second insufflator 14 is configured for insufflating the cavity 7. The first and second gases may be the same or different, depending on which of the two modes in which the apparatus 1 is being operated. As will be described below in a first mode of operation of the apparatus 1 the first and second gases are different, and in a second mode of operation of the apparatus 1 the first and second gases may be the same or different, but typically are the same.

A first pressure sensing means, in this embodiment of the invention a first pressure sensor 15 located in the housing 10 is configured to monitor the pressure of the first gas in the hollow organ 3, and to produce signals indicative of the static pressure in the hollow organ 3. A second pressure sensing means, in this embodiment of the invention a second pressure sensor 16 also located in the housing 10 is configured to monitor the pressure of the gases in the cavity 7, and to produce signals indicative of the static pressure in the cavity 7.

A gas detecting means, in this embodiment of the invention a side-stream gas detector 18 is located in the housing 10 for side-stream sampling gases exhausted from the one of the hollow organ 3 and the cavity 7, which is being insufflated with the second gas, and which in this embodiment of the invention is the cavity 7. The gas detector 18 is configured for detecting the presence of the first gas in the gases exhausted from the cavity 7 when the apparatus 1 is being operated in the first mode for detecting a leak through the sutured site 5 of the hollow organ 3, and for determining the size of the leak, as will be described below. The gas detector 18 is provided with a suction pump (not shown) which is configured to continuously sample the exhaust gases from the cavity 7 at a constant rate of 200 ml per minute. The gas detector 18 is configured to determine the concentration of the first gas in the gases exhausted from the cavity 7, and to produce signals indicative of the concentration of the first gas in the exhaust gases exhausted from the cavity 7.

The first insufflator 12 comprises a pressurised source of the first gas, namely, a first gas source 20. The first gas is supplied from the first gas source 20 through a first solenoid operated isolating valve 22 to a first pressure control means, namely, a first pressure regulator 21, which as will be described below controls the pressure at which the first gas is delivered to the hollow organ 3. The pressure controlled first gas is delivered from the first pressure regulator 21 through a flow sensing means, in this embodiment of the invention a flow meter 25, and in turn to the hollow organ 3 through a first delivery conduit 23. The flow meter 25 is located in the housing 10 and monitors the flow rate of the first gas through the first delivery conduit 23 as it is being delivered to the hollow organ 3.

The second insufflator 14 comprises a pressurised source of the second gas, namely, a second gas source 27. The second gas is supplied from the second gas source 27 through a second solenoid operated isolating valve 28 to a second pressure control means, namely, a second pressure regulator 29, which as will be described below controls the pressure at which the second gas is delivered to the cavity 7. A second delivery conduit 30 from the second pressure regulator 29 delivers the pressure controlled second gas from the second gas source to the cavity 7 for insufflating the cavity 7. The second delivery conduit 30 extends into the cavity 7 through the first trocar 8.

The first pressure sensor 15 is configured to monitor the static pressure in the hollow organ 3 through a first static pressure conduit 32 which communicates the first pressure sensor 15 with the interior of the hollow organ 3. Depending on the nature of the hollow organ, the first delivery conduit 23 and the first static pressure conduit 32 typically are entered into the organ through a normal inlet to or a normal outlet from the hollow organ 3. For example, in the event of the hollow organ 3 being the stomach of the subject, typically the first delivery conduit 23 and the first static pressure conduit 32 would be entered into the stomach through the oesophagus, either transorally or transnasally. On the other hand, in the event of the hollow organ 3 being the rectum, the colon, or the intestine the first delivery conduit 23 and the first static pressure conduit 32 would be inserted into the rectum, the colon or the intestine through the anus.

It is also envisaged that the first pressure sensor 15 could be configured to monitor the pressure in the hollow organ 3 through the first delivery conduit 23. However, in order to obtain a precise reading of the static pressure in the hollow organ 3, delivery of the first gas through the first delivery conduit 23 would have to be temporarily interrupted while the first pressure sensor 15 is monitoring the static pressure in the hollow organ 3 through the first delivery conduit 23. Alternatively, the dynamic pressure of the first gas in the first delivery conduit 23 could be continuously monitored, and a conversion factor for converting the dynamic pressure to the static pressure of the first gas in the hollow organ 3 could be provided, so that the static pressure of the first gas in the hollow organ 3 could be computed by applying the conversion factor to the monitored dynamic pressure.

A second static pressure conduit 34 communicates the second pressure sensor 16 with the cavity 7 through the second trocar 9, and the second pressure sensor 16 monitors the static pressure in the cavity 7 through the second static pressure conduit 34. However, it will be appreciated that the second pressure sensor 16 could monitor either the dynamic pressure of the second gas in the second delivery conduit 30, or the static pressure in the cavity through the second delivery conduit 30 in a similar manner as described with reference to the first pressure sensor 15 monitoring the pressure in the hollow organ 3 through the first delivery conduit 23.

A communicating conduit 35 extending from the one of the hollow organ 3 and the cavity 7 which is being insufflated with the second gas, and which in this embodiment of the invention is the cavity 7, communicates the gas detector 18 with the cavity 7 as will be described below, and terminates in a first exhaust port 40 through which the exhaust gases from the cavity 7 are exhausted to room air. The communicating conduit 35 is accommodated into the cavity 7 through the second trocar 9. Alternatively, the communicating conduit 35 and the static pressure conduit 34 may be entered into the cavity 7 through one or more veress needles, or through any other suitable means. The communicating conduit 35 is of internal diameter sufficiently large to reduce resistance to the flow of the exhaust gases flowing therethrough and to avoid any danger of a build-up of pressure in the cavity 7 as gas is being exhausted from the cavity 7 through the communicating conduit 35.

A T-connector 38 is located in the communicating conduit 35 upstream from the first exhaust port 40 for connecting the gas detector 18 to the communicating conduit 35. The gas detector 18 is connected to the T-connector 38 through a first connecting conduit 39, a first valving means, namely, a first valve 37 and a second connecting conduit 42 for facilitating sampling of the exhaust gases passing through the communicating conduit 35. The first valve 37 comprises a solenoid operated diverting valve selectively and alternately operable in a first state for communicating the gas detector 18 with the communicating conduit 35 for sampling the exhaust gases passing therethrough, and a second state for communicating the gas detector 18 with an inlet port 47 communicating with room air for purging the gas detector 18 as will be described below. An outlet conduit 45 from the gas detector 18 accommodates exhaust gas samples from the gas detector 18 to an outlet port 48 through which the exhaust gas samples are exhausted to room air.

A passive one-way valve 46 located in the communicating conduit 35 between the T-connector 38 and the first exhaust port 40 is configured to permit the flow of exhaust gases from the communicating conduit 35 through the first exhaust port 40, but to prevent gas flow in the reverse direction from the first exhaust port 40 to the T-connector 38, in order to avoid any danger of air being drawn through the exhaust port 40 and into the gas detector 18 by the suction pump (not shown) of the gas detector 18 in the event of the flow rate of exhaust gases through the communicating conduit 35 temporarily falling below 200 ml per minute. Since the sampling rate of the gas detector 18 is 200 ml per minute, if the flow rate of the exhaust gases through the communicating conduit 35 were to fall below 200 ml per minute, the pressure at the T-connector 38 would become negative, and thus without the passive one-way valve 46 air would be drawn in through the first exhaust port 40 into the gas detector 18. This would result in spurious results being produced by the gas detector 18. Instead of providing the passive one-way valve 46 between the exhaust port 40 and the T-connector 38, the length of the portion of the communicating conduit 35 between the T-connector 38 and the first exhaust port 40 may be increased to be of sufficient length, for example, 1 metre in order to provide a buffer for the exhaust gases from which the exhaust gases would be drawn by the gas detector 18, before any air would be mixed with the exhaust gases sampled by the gas detector 18, during the temporary fall in the flow rate of the exhaust gases below 200 ml per minute.

The first trocar 8 is provided with a second exhaust port 51 for exhausting the cavity 7 to room air. A manually operated valve 52 is located upstream of the second exhaust port 51, and is operable between an open state for exhausting gases from the cavity 7 through the second exhaust port 51 and a closed state closing the second exhaust port 51. A second valving means in this embodiment of the invention a normally closed solenoid operated second valve 53 is located downstream of the manual valve 52. By leaving the manual valve 52 in its open state, the second exhaust port 51 of the first trocar 8 may be selectively and alternately opened and closed by operating the second valve 53 remotely by the leak detecting apparatus 1 as will be described in more detail below. In the open state the second valve 53 communicates the second exhaust port 51 with a third exhaust port 54 from the second valve 53 for exhausting the cavity 7 therethrough.

A control means for controlling the operation of the apparatus 1, in this embodiment of the invention comprises a signal processor, provided in this case by a microprocessor 50. The microprocessor 50 is configured to control the operation of the first solenoid operated isolating valve 22 and the first pressure regulator 21 for controlling the delivery and the pressure at which the first gas is delivered to the hollow organ 3. The microprocessor 50 is also configured to control the operation of the second solenoid operated isolating valve 28 and the second pressure regulator 29 for controlling the delivery and the pressure at which the second gas is delivered to the cavity 7. The microprocessor 50 is also configured to control the operation of the first valve 37 as will be described below. Additionally, the microprocessor 50 is configured to remotely control the second valve 53 of the first trocar 8 for in turn controlling exhausting of the cavity 7 through the second exhaust port 51 of the first trocar 8 and the third exhaust port 54, as will also be described below.

The microprocessor 50 is configured to read signals from the first pressure sensor 15 which are indicative of the static pressure in the hollow organ 3, and to read signals from the second pressure sensor 16 which are indicative of the static pressure in the cavity 7. Additionally, the microprocessor 50 is configured to read signals from the gas detector 18 which are indicative of the concentration of the first gas detected in the gases exhausted from the cavity 7 through the communicating conduit 35. The microprocessor 50 is also configured to read signals from the flow meter 25 which are indicative of the flow rate at which the first gas is being delivered to the hollow organ 3 through the first delivery conduit 23. An interface 55 communicates with the microprocessor 50. The interface 55 may be a keypad, a touch screen, or a connector which would be suitable for connecting the microprocessor 50 to a laptop computer or a personal computer for inputting data to the microprocessor 50, as will be described below.

The microprocessor 50 is programmed to detect the presence of a leak in the hollow organ 3, when the apparatus 1 is operating in the first mode, from the signals read by the microprocessor 50 from the gas detector 18, and when the apparatus 1 is operating in the second mode, from the signals read by the microprocessor 50 from the flow meter 25, as will be described below. Additionally, the microprocessor 50 is programmed as a computing means for computing the size of the leak in the hollow organ 3. When the apparatus 1 is operating in the first mode, the microprocessor 50 is programmed to compute the size of the leak in the hollow organ 3 from the signals read from the gas detector 18 and from the signals read from the first and second pressure sensors 15 and 16, as will be described below. When the apparatus 1 is operating in the second mode, the microprocessor 50 is programmed to compute the size of the leak in the hollow organ 3 from the signals read from the flow meter 25 and from the signals read from the first and second pressure sensors 15 and 16 as will also be described below.

In order to fully understand the apparatus 1, the method for operating the apparatus 1 in the first and second modes will now be described for detecting a leak and for determining the size of the leak in the hollow organ 3 to the cavity 7. When operating in the first mode, the apparatus 1 is configured to compute the size of the leak through the sutured site 5 of the hollow organ 3 as a function of the pressure differential between the pressure in the hollow organ 3 and the pressure in the cavity 7, which is lower than the pressure in the hollow organ 3, and the concentration of the first gas detected in the gases exhausted from the cavity 7. When operating in the second mode, the apparatus is configured to compute the size of the leak through the sutured site 5 of the hollow organ 3 as a function of the pressure 10) differential between the pressure in the hollow organ 3 and the pressure in the cavity 7, which is lower than the pressure in the hollow organ 3, and the flow rate of the first gas being delivered through the first delivery conduit 23 to the hollow organ 3.

In order that the first gas can be detected in the exhaust gases from the cavity 7 when the apparatus 1 is operating in the first mode, the first gas must be different to the second gas. In this embodiment of the invention, in both the first and second modes of operation of the apparatus 1, the second gas provided by the second gas source 27 is carbon dioxide gas, which is a gas commonly used for insufflating a cavity in a human or animal subject. In the first mode of operation of the apparatus 1, in order that the first gas which is detected in the gases exhausted from the cavity 7 is the same first gas which is delivered into the hollow organ 3, as well as the first gas being different from the second gas, the first gas provided by the first gas source 20 should be a gas which does not normally occur in the hollow organ 3 or in the cavity 7 of the body of the human or animal subject, or if it does, it occurs in negligible amounts only. Preferably, the first gas should be a gas which does not occur in the body of a human or animal subject, or if it does, it occurs in negligible amounts only. In this embodiment of the invention, when the apparatus 1 is to be operated in the first mode, the first gas which is provided by the first gas source 20 is nitrous oxide gas ($N_2O$). Thus, in the first mode of operation of the apparatus 1, the gas detector 18 is configured for detecting nitrous oxide gas. When the apparatus 1 is to operate in the second mode the first gas is carbon dioxide gas, although in the second mode of operation of the apparatus 1 the first gas may be the same or different to the second gas.

Prior to operation of the apparatus 1 in either the first or the second mode the apparatus 1 is operated as a normal insufflator for insufflating the cavity 7 while the surgical procedure is being carried out on the hollow organ 3. During the operation of the apparatus 1 as an insufflator while the surgical procedure on the hollow organ 3 is being carried out, the microprocessor 50 is programmed to only operate the second insufflator 12 for insufflating the cavity 7. The microprocessor 50 reads signals from the second pressure sensor 16, and controls the second pressure regulator 23 to maintain the pressure of the second gas supplied to the cavity 7 at the desired insufflating pressure to provide access to the hollow organ 3. On completion of the procedure, when it is desired to test the sutured site 5 of the hollow organ 3 for leaks, the apparatus 1 is operated in either the first mode or the second mode.

In both the first and second modes of operation of the apparatus 1 for testing the sutured site 5 of the hollow organ 3 for leaks, the microprocessor 50 is programmed to read the signals from the first and second pressure sensors 15 and 16 and to operate the first and second insufflators 12 and 14 to insufflate the hollow organ 3 and the cavity 7, respectively. Typically, during operation of the apparatus 1 in the first and second modes of operation, the microprocessor 50 is programmed to control the second insufflator 14 to reduce the insufflating pressure in the cavity 7 to a predefined pressure value, which is just sufficient to maintain the cavity insufflated. Typically, the predefined pressure value lies in the range of 5 mmHg to 10 mmHg, and ideally, as close as possible to 5 mmHg. The microprocessor 50 controls the second pressure regulator 29 to maintain the pressure in the cavity 7 at the appropriate predefined pressure value during the period when the apparatus 1 is operating in both the first and second modes. When the apparatus 1 is operating in both the first and second modes, the microprocessor 50 then operates the first insufflator 12 to deliver the first gas into the hollow organ 3, and the microprocessor 50 controls the first pressure regulator 21 to increase and maintain the pressure of the first gas in the hollow organ 3 relative to the pressure in the cavity 7 in order to maintain a pressure differential between the pressure in the hollow organ 3 and the pressure in the cavity 7 constant at a predefined pressure differential value in the range of 3 mmHg to 12 mmHg, and preferably, at a value of approximately 7 mmHg, with the pressure in the hollow organ 3 above the pressure in the cavity 7. Maintaining the pressure in the cavity 7 constant at the predefined pressure in the range of 5 mmHg to 10 mmHg should avoid any danger of over pressurising the hollow organ 3.

The predefined pressure value is selectable, and is inputted to the microprocessor 50 through the interface 55. The predefined pressure differential value is also selectable and is inputted to the microprocessor 50 through the interface 55.

In the first mode of operation of the apparatus 1, with the second pressure regulator 29 maintaining the pressure in the cavity constant at the predefined pressure value, and with the first pressure regulator 21 maintaining the pressure differential between the pressure in the hollow organ 3 and the lower pressure in the cavity 7 constant at the predefined pressure differential value, on commencement of delivery of the first gas from the first insufflator 12 to the hollow organ 3, the microprocessor 50 is programmed to time a predefined time period commencing at the commencement of the delivery of the first gas by the first insufflator 12 to the hollow organ 3. The predefined time period may be of any suitable time duration, and typically, would lie in the range of 10 seconds to 60 seconds, but may be longer or shorter. Although preferably, the predefined time period would lie in the range of 30 seconds to 60 seconds. In this embodiment of the invention the predefined time period is approximately 60 seconds. The duration of the predefined time period is selectable, and is inputted to the microprocessor 50 through the interface 55.

During the predefined time period, the microprocessor 5 is programmed to read the signals from the gas detector 18, which are indicative of the concentration of the first gas in the exhaust gases exhausted from the cavity 7, at predefined sampling time intervals. The microprocessor 50 logs and time stamps the respective values of the concentration of the first gas in the gases exhausted from the cavity 7 read from the gas detector 18 at the end of each predefined sampling time interval. The predefined sampling time intervals may be of any suitable time duration, and the time duration of each predefined sampling time interval will be to some extent dependent on the time duration of the predefined time period. However, in general, the time duration of each predefined sampling time interval will lie in the range of 0.01 seconds to 2 seconds, and preferably, will lie in the range of 0.5 seconds to 1 second. In this embodiment of the invention the duration of the predefined sampling time intervals is approximately 1 second. The duration of the predefined sampling time intervals is selectable, and is inputted to the microprocessor 50 through the interface 55.

As the predefined time period is about to time out, the microprocessor 50 logs a final reading of the concentration of the first gas in the gases exhausted from the cavity 7. On the predefined time period having timed out, the microprocessor 50 then computes the size of the leak as a function of the predefined pressure differential value between the pressure in the hollow organ 3 and the pressure in the cavity 7, and either the final read value concentration of the first gas in the gases exhausted from the cavity 7, or the rate of change of the concentration of the first gas in the exhaust gases from the cavity 7 either during the predefined time period, or towards the end of the predefined time period, or the integral of the concentration of the first gas in the exhaust gases with respect to time during the predefined period or a selected part thereof.

Accordingly, in the embodiment of the invention where the size of the leak through the sutured site 5 of the hollow organ 3 is computed as a function of the final value of concentration of the first gas in the gases exhausted from the cavity 7 at the end of the predefined time period, the microprocessor 50 is programmed to compute the size of the leak based on the following equation:

$$y = K \cdot x \cdot \Delta p \tag{1}$$

where
  y is the leak size,
  x is the final value of the concentration of the first gas in the exhaust gases from the cavity 7 at the end of the predefined time period,
  $\Delta p$ is the predefined pressure differential value, and
  K is a constant empirically derived.

In the embodiment of the invention where the size of the leak through the sutured site 5 in the hollow organ 3 is computed as a function of the rate of change of the concentration of the first gas in the gases exhausted from the cavity 7 during the predefined time period, the microprocessor 50 is programmed to compute the size of the leak based on the following equation:

$$y = K \cdot dx/dt \cdot \Delta p \tag{2}$$

where
  y is the leak size,
  dx/dt is the rate of change of the concentration of the first gas in the gases exhausted from the cavity 7 with respect to time during the predefined time period,
  $\Delta p$ is the predefined pressure differential value, and
  K is a constant empirically derived.

In the embodiment of the invention where the size of the leak through the sutured site 5 of the hollow organ 3 is computed as a function of the integral of the values of the concentration of the first gas in the gases exhausted from the cavity 7 at the end of each predefined sampling time interval during the predefined time period, or during a selected part of the predefined time period, the microprocessor is programmed to compute the size of the leak based on the following equation:

$$y = K \cdot \Delta p \cdot \int_{t=0}^{t=T} x \cdot dt \tag{3}$$

where
  y is the leak size,
  t is the time at the end of each predefined sampling time interval from the commencement of the predefined time period or from the commencement of the selected part of the predefined time period, at which the values of the concentration of the first gas in the gases exhausted from the cavity 7 are read by the microprocessor 50 from the gas detector 18,
  x is the value of the concentration of the first gas in the gases exhausted from the cavity 7 at time t from the commencement of the predefined time period or from the commencement of the selected part thereof,
  T is the time duration of the predefined time period or the selected part thereof during which the test is being carried out,
  $\Delta p$ is the predefined pressure differential value, and
  K is a constant empirically derived.

On completion of the test for the leak through the sutured site 5 in the hollow organ 3, and in a case where a leak has been detected, and the size of the leak is determined to be of size necessitating further repair of the defective part of the sutured site 5, the repaired sutured site 5 must be retested for leaks after the repair has been carried out. Prior to retesting, the cavity 7 and the apparatus 1 must first be purged of the first gas.

Purging of the cavity 7 and the apparatus 1 is carried out under the control of the microprocessor 50, which operates the apparatus 1 to carry out a purging cycle. During the purging cycle, the microprocessor 50 is programmed to operate the second insufflator 14 to deliver the second gas into the cavity 7 in order to purge the cavity 7 of the first gas. Initially, during purging of the cavity 7 with the second gas, with the manual exhaust valve 52 of the first trocar 8 in the open state, the second valve 53 is operated by the microprocessor 50 into the open state to exhaust the gases from the cavity 7 through the third exhaust port 54, and is maintained in the open state by the microprocessor 50 for a sufficient time to fully purge the cavity 7 to remove the first gas therefrom. The second valve 53 is then operated by the microprocessor 50 into the closed state, and the second gas continues to be delivered into the cavity 7 by the second insufflator 14. The second gas then continues from the cavity 7 and in turn through the communicating conduit 35, and is exhausted through the first exhaust gas port 40, and also through the gas detector 18 with the first value 37 in the first state communicating the gas detector 18 with the communicating conduit 35 for purging thereof. Towards the end of this part of the purging cycle, the microprocessor 50 operates the first valve 37 into the second state to communicate the gas detector 18 with the inlet port 47, and the gas detector 18 is operated to draw room air in through the inlet port 47 to further purge the gas detector 18. The purging cycle continues for a suitable period of time until the first gas from the previous test has been fully purged from the cavity 7 and from the apparatus 1.

At the end of the purging cycle the effectiveness of the purging cycle is checked. The first valve 37 is operated by the microprocessor 50 into the first state communicating the gas detector 18 with the communicating conduit 35. With the second valve 53 in the closed state, the second insufflator 14 is operated to deliver the second insufflating gas into the cavity 7 through the second delivery conduit 30 and from the cavity 7 through the communicating conduit 35 for sampling by the gas detector 18. The microprocessor 50 reads the signals from the gas detector 18 to determine if the cavity 7 and the apparatus 1 have been fully purged of the first gas, or if not fully purged, the concentration of the first gas in the gases exhausted from the cavity 7 and in the apparatus 1 has been reduced to an acceptable level, for example, in the order of 1% to 2%, and thus the cavity 7 and the apparatus 1 have been adequately purged. If the purging cycle has been unsuccessful in purging the first gas from the cavity 7 and the apparatus 1, the purging cycle is repeated.

Once the purging cycle has been completed, and the cavity 7 and the apparatus 1 are free of the first gas, the apparatus 1 is operated in the first mode as already described for again detecting if the repaired sutured site 5 has been fully sealed, and if not to determine the size of the leak from the repaired sutured site 5. Needless to say, if further repairing is required, the purging cycle is repeated. After a further repair has been carried out, the apparatus 1 is then again operated in the first mode for again testing the repaired sutured site 5 for leaks and the size thereof.

Turning now to the operation of the apparatus 1 in the second mode for detecting a leak and determining the size of the leak through a sutured site 5 in a hollow structure, for example, the hollow organ 3 in the cavity 7 in the body of a human or animal subject. In the second mode of operation of the apparatus 1, the first and second gases as discussed above typically are the same. In this case, both the first gas and the second gas are carbon dioxide, and in this embodiment of the invention both could be derived from a single gas source of carbon dioxide, instead of providing first and second gas sources. Additionally, in the second mode, the gas detector is not required, and it is therefore not necessary to provide the communicating conduit 35 from the cavity 3 to the apparatus 1, which may be omitted, and the gas from the cavity 7 may be discharged through any suitable discharge means, for example, through the exhaust outlet 51 in the first trocar 8, through a veress needle, or through the second trocar 9 or by any other suitable means. However, in the second mode, the microprocessor 50 is programmed to read the signals from the flow meter, and to determine the flow rate of the first gas from the first insufflator 12 to the hollow organ 3.

During operation of the apparatus 1 in the second mode, the microprocessor 50 as already described with respect to the operation of the apparatus 1 in the first mode reads signals from the first pressure sensor 15 and the second pressure sensor 16, and controls the second pressure regulator 29 to maintain the pressure in the cavity 7 constant at the predefined pressure value as already described. The microprocessor 50 then controls the first pressure regulator 21 to control the pressure in the hollow organ 3 in order to maintain the pressure differential between the pressure in the hollow organ 3 and the lower pressure in the cavity 7 constant at the predefined pressure differential value as already described. Both the desired predefined pressure value and the desired predefined pressure differential value are inputted to the microprocessor 50 through the interface 55.

In order to detect the presence of a leak from the sutured site 5 in the hollow organ 3 and the size of the leak, the microprocessor 50 is programmed to read signals from the flow meter 25. Assuming that apart from the sutured site 5 the hollow organ 3 can be and is sealed, if the microprocessor 50 determines from the signals read from the flow meter 25 that the first gas continues to flow from the first insufflator 12 through the first delivery conduit 23 to the hollow organ 3 once the differential pressure between the hollow organ 3 and the cavity 7 has been established at the constant predefined pressure differential value, and the hollow organ apart from the sutured site 5 is sealed, the microprocessor 50 is programmed to confirm the detection of a leak. The microprocessor 50 is programmed to then compute the size of the leak as a function of the predefined pressure differential value between the hollow organ 3 and the cavity 7, and the flow rate of the first gas through the first delivery conduit 23 to the hollow organ 3, which is determined by the microprocessor 50 from signals read from the flow meter 25. The microprocessor 50 computes the size of the leak based on the following equation:

$$y = K \cdot x \cdot \Delta p \qquad (4)$$

where
  y is the computed size of the leak,
  x is the value of the flow rate of the first gas determined from the signals read from the flow meter 25 by the microprocessor 50 after the pressure differential between the pressures in the hollow organ 3 and the cavity 7 has been established to be constant at the predefined pressure differential value,
  $\Delta p$ is the predefined pressure differential value, and
  K is a constant derived empirically.

It will be appreciated that when the apparatus is being operated in the second mode, and the size of the leak is computed as a function of the flow rate of the first gas to the hollow organ, and in turn the flow rate of the first gas through the sutured site of the hollow organ, if the hollow organ is not sealed apart from the sutured site, the flow rate of the first gas determined from the flow meter will not give a true reading of the flow rate of the first gas through the sutured site, since the first gas will leak from other orifices to and from the hollow organ. Therefore, in cases where a hollow organ is not sealed apart from the sutured site, for example, in the case of the stomach, the large or small intestine, the colon and the rectum, where the first gas could leak from the relevant hollow organ through the mouth or the anus, or through both, it is essential that all other orifices from the hollow organ must be sealed apart from the sutured site. In the case of the digestive track, sealing of the stomach at both ends thereof can be readily carried out by inflating an inflatable balloon in the oesophagus adjacent the stomach and inflating an inflatable balloon in the small intestine adjacent the stomach, with these two balloons inflated, both the entry and exit from the stomach would be sealed. Similarly, in the case of the large or small intestine, two inflatable balloons would be inflated in the intestine at opposite ends of the sutured site, in order to seal the portion of the intestine adjacent the sutured site. Similarly, in the case of the colon, two inflatable balloons would be inflated in the colon at opposite ends of the sutured site to seal the colon adjacent the sutured site. In the case of the rectum, two inflated balloons, one in the colon adjacent the rectum and the other in the anus would seal the rectum. It is envisaged that in these cases the balloons would be provided appropriately spaced apart on a single lumen or a multi-lumen balloon catheter, and the necessary communicating access to the hollow organ would be provided through the lumen or lumens of the catheter as appropriate.

If a leak is detected from the hollow organ 3 and the size of the leak is such as to require further repair of the sutured site 5, on completion of the repair, the sutured site 5 is again tested for leaks. However, when the apparatus 1 is operating in the second mode, there is no need to purge the cavity 7 or the apparatus 1 between tests of the sutured site 5, since the first and second gases are the same. However, even if the first and second gases were different, there would still be no need to purge the cavity 7 and the apparatus 1, between tests of the sutured site 5 for leaks between repairs thereof, when the apparatus is operating in the second mode, since in the second mode of operation of the apparatus 1, only the flow rate of the first gas and the pressure differential value between the pressures in the hollow organ 3 and the cavity 7 are required to determine the size of the leak through the sutured site in the hollow organ 3.

Referring now to FIG. 2 there is illustrated a leak detecting apparatus according to another embodiment of the invention indicated generally by the reference numeral 60 for detecting a leak and the size of the leak through a sutured site, for example, a sutured site 62 in a hollow structure, such as a lumen or a hollow organ 63 in a cavity 65 in the body of a human or animal subject, after a surgical procedure, typically of the type carried out by micro-surgery or laparoscopic surgery. The apparatus 60 is substantially similar to the leak detecting apparatus 1 described with reference to FIG. 1, and similar components are identified by the same reference numerals. The main difference between the apparatus 60 and the apparatus 1 described with reference to FIG. 1 is that the second insufflator together with the second insufflating gas source, the second isolating valve and the second pressure regulator have been omitted from the apparatus 60. Accordingly, the apparatus 60 is suitable for use in conjunction with an external insufflator, which typically would be a conventional insufflator, and which would fulfil the functions of the second insufflator of the apparatus 1.

In FIG. 2 the apparatus 60 is illustrated in conjunction with an external insufflator 66 which acts as a second insufflator. The external insufflator 66 is configured to insufflate the cavity 65 with an insufflating gas, namely, the second gas, typically, carbon dioxide. The external insufflator 66 essentially operates in place of the second insufflator 14. Only the essential elements of the external insufflator 66 are illustrated. The external insufflator 66 comprises a housing 68 within which the components thereof are housed. An insufflating gas source 69 is located in the housing 68 and provides a supply of the second gas to a pressure control means, in this case a pressure regulator 70 which is also located in the housing 68. The insufflating gas from the insufflating gas source 69 is supplied to the pressure regulator 70 through a solenoid operated isolating valve 64, namely, a second isolating valve, also located in the housing 68. The second insufflating gas at a suitable pressure controlled by the pressure regulator 70 is supplied to the cavity 65 through an insufflating gas delivery conduit 67 through a first trocar 71 similar to the first trocar 8 described with reference to FIG. 1.

Additionally, in this embodiment of the invention the static pressure conduit 34 from the second pressure sensor 16 and the communicating conduit 35 are entered into the cavity 65 through a second trocar 72, which is similar to the second trocar 9 described with reference to the apparatus 1.

The operation of the external insufflator 66 is controlled by an on-board suitable signal processor, for example, a microprocessor 74 which is located in the housing 68, and controls the operation of the second isolating valve 64 and the pressure regulator 70 in order to insufflate the cavity 65 to a desired pressure.

In this embodiment of the invention, the microprocessor 50 of the apparatus 60 communicates with the microprocessor 74 of the external insufflator 66 through a communicating means, in this case a hardwired communication path 73, so that on completion of the surgical procedure on the hollow organ 63, the external insufflator 66, which maintains the cavity 65 insufflated during the surgical procedure, can be controlled by the microprocessor 50 of the apparatus 60 to instruct the external insufflator 66 to insufflate the cavity 65 and to set and maintain the pressure in the cavity 7 at the appropriate selected predefined pressure value in the range of 5 mmHg to 10 mmHg, in order to test the efficacy of the sutured site 62. Accordingly, during testing of the efficacy of the sutured site 62 the apparatus 60 in conjunction with the external insufflator 66 operates in a substantially similar manner to that described with reference to the apparatus 1 of FIG. 1. The first insufflator 12 is operated to deliver the first gas to the hollow organ 63, while the external insufflator 66 under the control of the microprocessor 50 is operated in a similar manner as that of the second insufflator 14 of the apparatus 1 to deliver the insufflating gas, namely, a second gas from the insufflating gas source 69 to the cavity 65 for insufflating the cavity 65 and for maintaining the pressure in the cavity 65 at the appropriate predefined pressure value. The apparatus 60 in conjunction with the external insufflator 66 may be operated in a first mode or a second mode which are similar to the first and second modes, respectively, of operation of the apparatus 1 for detecting a leak and the size thereof in the hollow organ 63.

During operation of the apparatus 60 in the first mode, on completion of the procedure carried out on the hollow organ 3, the microprocessor 50 of the apparatus 60 directs the external insufflator 66 to continue to insufflate the cavity 65, but at a reduced pressure, namely, at the appropriate selected predefined pressure value in the range of 5 mmHg to 10 mmHg. A suitable first gas different to the second gas of the insufflating gas source 69 of the external insufflator 66 is delivered into the hollow organ 63 by the first insufflator 12. The microprocessor 50 of the apparatus 60 reads the pressure signals from the first pressure sensor 15 indicative of the pressure in the hollow organ 63, and reads signals from the second pressure sensor 16, which are indicative of the pressure in the cavity 65. The microprocessor 50 of the apparatus 60 controls the first isolating valve 22 and the first pressure regulator 21 for maintaining the pressure in the hollow organ 63 constant at the appropriate selected predefined pressure differential value of preferably 7 mmHg above the pressure in the cavity 65. The microprocessor 50 reads signals from the gas detector 18 and computes the size of the leak as already described with reference to the operation of the apparatus 1.

When the apparatus 60 is being operated in the second mode, the microprocessor 50 reads signals from the flow meter 25 and from the first and second pressure sensors 15 and 16, and computes the size of the leak as a function of the flow rate of the first gas to the hollow organ 3 and the constant predefined pressure differential value as already described with reference to the operation of the apparatus 1 in the second mode. When the apparatus 60 is operating in the second mode, the first gas may be similar to the second gas.

Otherwise, the operation of the apparatus 60 in conjunction with an external insufflator 66 is similar to that of the apparatus 1 described with reference to FIG. 1, as is the operation of the apparatus 60 for purging the cavity 65 and the apparatus 60 of the first gas to that already described with reference to the apparatus 1.

Referring now to FIG. 3 there is illustrated a leak detecting apparatus according to another embodiment of the invention indicated generally by the reference numeral 75 for detecting a leak from a sutured site, for example, a sutured site similar to the sutured site 62 in a hollow organ, similar to the hollow organ 63 in a cavity 65 in the body of a human or animal subject as described with reference to FIG. 2. The apparatus 75 is substantially similar to the leak detecting apparatus 60, and similar components are identified by the same reference numerals. In this embodiment of the invention the apparatus 75, like the apparatus 60 is provided without a second insufflator, and like the apparatus 60, the apparatus 75 is provided to operate in conjunction with an external insufflator 76. However, unlike the apparatus 60, the apparatus 75 is not provided to control the external insufflator 76, and the hardwired communication path between the microprocessor 50 of the apparatus 75 and the microprocessor 74 of the external insufflator 76 has been omitted. In this embodiment of the invention the external insufflator 76 is provided for insufflating the cavity 65 during the procedure on the hollow organ 63 only, and is not required during testing of the efficacy of the sutured site 62 of the hollow organ 63, and is operated independently of the apparatus 75.

A diverting valve 77 is located in the insufflating gas delivery conduit 67 and is alternatively and selectively operated under the control of the microprocessor 50 of the apparatus 75 between a normal state communicating the external insufflator 76 with the cavity 65 and a diverting state for diverting the insufflating gas from the external insufflator 76 from the cavity 65 to a reservoir 78 during the period while the apparatus 75 is operating in either one of the first and second modes in order to maintain the pressure of the insufflating gas delivered by the external insufflator 76 at the normal operating pressure value. The reservoir 78, in this embodiment of the invention comprises an expandable reservoir, and ideally, is provided by a resiliently expandable balloon. The external insufflator 76 is of the type, which when the pressure of the insufflating gas being delivered to a cavity being insufflated falls below a predefined pressure value, the insufflator outputs an alerting signal, typically, an audible alarm. During the operation of the apparatus 75 in either of the first and second modes, when the external insufflator 76 is not required, in order to avoid having to deactivate the external insufflator 76 the diverting valve 77 is operated into the diverting state to divert the insufflating gas from the external insufflator 76 into the reservoir 78. The external insufflator 76 maintains the insufflating gas pressure at the normal insufflating gas pressure, thereby avoiding activation of the audible alarm of the external insufflator 76.

Accordingly, in use during the carrying out of the procedure on the hollow organ 63, the apparatus 75 remains inactive, and the cavity 65 is insufflated by the external insufflator 76 with the diverting valve 77 operated in the normal state under the control of the microprocessor 50 of the apparatus 75 for delivering the insufflating gas from the external insufflator 76 to the cavity 65.

On completion of the procedure on the hollow organ 63, to operate the apparatus 75 in either the first or the second mode, the external insufflator 76 continues to operate, and the diverting valve 77 is operated by the microprocessor 50 of the apparatus 75 into a diverting state for diverting the insufflating gas from the external insufflator 76 into the reservoir 78. Prior to operating the diverting valve 77 into the diverting state, the external insufflator 76 may be operated to reduce the pressure in the cavity 65 to an appropriate predefined pressure value in the range of 5 mmHg to 10 mmHg for enabling carrying out of the test to test the efficacy of the sutured site 62 of the hollow organ 63. Alternatively, after the diverting valve 77 has been operated into the diverting state, the second valve 53 downstream of the exhaust port 51 of the first trocar 71 may be operated into the open state under the control of the microprocessor 50 of the apparatus 75 in order to reduce the pressure in the cavity 65 to the appropriate predefined pressure value in the range of 5 mmHg to 10 mmHg to similarly allow the test of the efficacy of the sutured site 62 of the hollow organ 63. Once the pressure in the cavity 65 has been reduced to the appropriate predefined pressure value, the apparatus 75 is operated to carry out the test of the efficacy of the sutured site 62 of the hollow organ 63.

When the apparatus 75 is operated in the first mode, the microprocessor 50 of the apparatus 75 reads signals from the first and second pressure sensors 15 and 16, and operates the first insufflator 12 to deliver the first gas into the hollow organ 63 in order to control the pressure in the hollow organ 63 for maintaining the pressure differential between the pressure in the hollow organ 63 and the pressure in the cavity 65 constant at the appropriate selected predefined pressure differential value, preferably of 7 mmHg above the pressure in the cavity 65. Immediately upon commencement of the delivery of the first gas by the first insufflator 12 to the hollow organ 63, timing of the predefined time period commences, and the gas detector 18 commences to sample the concentration of the first gas in the exhausted gases from the cavity 65. Thereafter, operation of the apparatus 75 in the first mode of operation for computing the size of the leak from the sutured site 62 of the hollow organ 63 is similar to that already described with reference to the apparatus 1 and 60.

When the apparatus 75 is operated in the second mode, as discussed above the first gas may be a gas different to the insufflating gas supplied by the external insufflator 76, or the first gas may be the same as the insufflating gas supplied by the external insufflator 76 to the cavity 65. In the second mode of operation of the apparatus 75, the microprocessor 70 reads signals from the first and second pressure sensors 15 and 16, and operates the first insufflator 12 to maintain the pressure differential between the hollow organ 63 and the cavity 65 constant at the predefined pressure differential value preferably of 7 mmHg above the pressure in the cavity 65. The microprocessor reads signals from the flow meter, and thereafter operation of the apparatus 75 in the second mode for computing the size of the leak from the sutured site 62 of the hollow organ 63 is similar to that already described with reference to the apparatus 1 and 60.

In this embodiment of the invention when the apparatus 75 is operating in either the first mode or the second mode, once the pressure in the cavity 65 has been reduced to the desired predefined pressure, and the insufflating gas from the external insufflator 76 has been diverted by the diverting valve 77 from the cavity 65 to the reservoir 78, the pressure in the cavity 65 will fall gradually. The microprocessor 50 of the apparatus 75 thus controls the first insufflator 12 to control the pressure of the first gas in the hollow organ 63 to maintain the pressure differential between the pressures in the hollow organ 63 and the cavity 65 constant at the predefined pressure differential value.

When the apparatus 75 is operated in the first mode, on completion of the operation of the apparatus 75 in the first mode, purging of the cavity 65 and the apparatus 75 in order to purge the first gas from both the cavity 65 and the apparatus 75 is carried out in a similar fashion as that described with reference to the apparatus 1 and 60. The diverting valve 77 is operated by the microprocessor 50 of the apparatus 75 into the normal state for communicating the external insufflator 76 with the cavity 65, and the external insufflator 76 is then operated to supply the second gas to the cavity 65 for purging thereof and for purging the apparatus 75.

Referring now to FIG. 4 there is illustrated a leak detecting apparatus according to a further embodiment of the invention indicated generally by the reference numeral 100. The apparatus 100 is substantially identical to the apparatus 1, and similar components are identified by the same reference numerals. The only difference between the apparatus 100 and the apparatus 1 is that the static pressure conduit 34 has been omitted, and the second pressure sensor 16 monitors the pressure in the cavity 7 through the second delivery conduit 30. In this embodiment of the invention the second pressure sensor 16 may be configured to monitor the dynamic pressure of the insufflating gas from the second insufflator 14 in the second delivery conduit 30, and a conversion factor would be stored in the microprocessor 50 for converting the dynamic pressure read from the second pressure sensor 16 to the static pressure in the cavity 7. Alternatively, the microprocessor 50 may be configured to periodically temporarily deactivate the second insufflator while the signals from the second pressure sensor 16 are read by the microprocessor 50, so that the signals read from the second pressure sensor 16 would be indicative of the static pressure in the cavity 7.

Otherwise, the apparatus 100 is similar to the apparatus 1, and its operation is likewise similar.

While in the description of the apparatus 1, 60 and 100, the apparatus have been described as being operated whereby the hollow organ is insufflated with the first gas by the first insufflator, and the cavity is insufflated with the second gas by the second insufflator or the external insufflator, as the case may be, it is envisaged that the apparatus 1, 60 and 100 may be operated in both the first and second modes whereby the first insufflator would insufflate the cavity with the first gas, and the second insufflator would insufflate the hollow organ with the second gas. In which case, the communicating conduit would be configured to exhaust the gases from the hollow organ, rather than from the cavity, and the gas detector would sample the exhaust gases being exhausted through the communicating conduit from the hollow organ. In these cases the first pressure sensor would monitor the pressure in the hollow organ and the second pressure sensor would monitor the pressure in the cavity as already described. The flow meter would monitor the flow rate of the first gas from the first insufflator to the cavity. When operating the apparatus 1, 60 and 100, when so configured, the microprocessor 50 of the apparatus, when operating the apparatus in the first or second modes would read signals from the first pressure sensor, and would control the second insufflator to insufflate the hollow organ with the second gas and to maintain the pressure of the second gas in the hollow organ at the predefined pressure value, typically, in the range of 5 mmHg to 10 mmHg, and ideally, as close as possible to 5 mmHg, in response to the signals read from the first pressure sensor. The microprocessor 50 would also read signals from the first and second pressure sensors, and would control the first insufflator to maintain the pressure of the first gas in the cavity in response to the signals read from the first and second pressure sensors in order to establish and maintain the pressure differential between the pressure in the cavity and the pressure in the hollow organ constant at the predefined pressure differential value, typically at 7 mmHg. When the apparatus is operating in this configuration, the pressure in the cavity will be maintained at a higher pressure than the pressure in the hollow organ.

When operating in the first mode in this configuration of the apparatus 1, 60 and 100, the microprocessor 50 would read signals from the gas detector and from the first and second pressure sensors, and would compute the size of a leak through a sutured or otherwise repaired site or a perforated site in the hollow organ from the signals read from the gas detector and from the pressure differential between the pressures in the cavity and the hollow organ from signals read from the first and second pressure sensors as described with reference to the operations of the apparatus 1, 60 and 100 when operating in the first mode. In the first mode of operation of the apparatus 1, 60 and 100 in this configuration, in the event of a leak in the sutured or otherwise repaired site in the hollow organ, the first gas would pass from the cavity through the sutured site in the hollow organ into the hollow organ.

When the apparatus 1, 60 and 100 in this configuration are operating in the second mode, the microprocessor 50 of the apparatus would compute the size of a leak through a sutured site in the hollow organ based on the flow rate of the first gas to the cavity from signals read from the flow meter and from the pressure differential between the pressure in the cavity and the pressure in the hollow organ.

Purging of the apparatus 1, 60 and 100 when operating in this configuration would be carried out by delivering the second gas into the hollow organ, and purging the first gas from the hollow organ and the apparatus.

Otherwise, operation of the apparatus 1, 60 and 100 in this configuration would be similar to the operation of the apparatus 1, 60 and 100 already described with reference to FIGS. 1, 2 and 4, whereby the first gas is delivered to the hollow organ and the second gas is delivered to the cavity, and the first gas is detected in the gases in or exhausted from the cavity.

While the communicating link 73 between the microprocessor 50 of the apparatus 60 and the microprocessor 74 of the external insufflator 66 of the apparatus 60 of FIG. 2 has been described as being a hardwired communication path, it will be readily apparent to those skilled in the art that the communicating means between the microprocessor 50 in the apparatus 60 and the microprocessor 74 of the external insufflator 66 could be by any other suitable communicating link, for example, a wireless communicating link, which could be carried out under a Bluetooth protocol, or any other suitable wireless communications protocol.

It is also envisaged that the microprocessors 50 and 74 of the apparatus 60 and the external insufflator 66 could be programmed so that the external insufflator 66 could be operated solely under the control of the microprocessor 50 during both the normal insufflation of the cavity during the carrying out of the surgical procedure on the hollow organ 63, and during operation of the external insufflator in conjunction with the apparatus 60 when operating the apparatus 60 in the first and second modes for testing a sutured site for a leak.

Although not illustrated or described, it is envisaged that the apparatus 1, 60, 75 and 100 will be provided with an alerting device, for example, an alerting device which will give a human perceptible signal, such as an audible alarm and/or a visual alarm in the event of either the signals produced by the first pressure sensor 15 and/or the second pressure sensor 16 of the apparatus 1, 60, 75 or 100 being indicative of the pressure in either the hollow organ or the cavity exceeding respective predefined safe operating pressures.

While the apparatus 1, 60, 75 and 100 have been described as being configured to operate in the two modes for detecting a leak and determining the size of the leak from a hollow organ, it is envisaged that any and all of the apparatus 1, 60, 75 and 100 may be configured to operate in one single mode only. For example, in a case where the apparatus is configured to operate in the first mode only, the flow meter may be omitted. On the other hand, in a case where the apparatus is configured to operate in the second mode only, the gas detector 18, as well as the first valve 37 and the communicating conduit 35 and the T-connector 38 would not be required, and would therefore be omitted.

While the first gas has been described as being nitrous oxide, it will be readily apparent to those skilled in the art that any other suitable first gas may be provided. However, where the first gas is to be detected by the gas detector, it will be readily apparent to those skilled in the art that the first gas must be detectable in the exhaust gases, and if the first gas is a gas which does occur naturally in either the hollow organ or the cavity of a subject, the normal background level of that gas in the cavity would have to be taken into account when determining the presence of a leak and determining the size of the leak.

However, ideally, the first gas should be a gas which is easily detectable in the gases exhausted from the cavity, and should be a gas which does not normally occur in the relevant hollow structure or cavity.

While the second valve 53 has been described as being provided on the exhaust port of the first trocars 8 and 71 downstream of the manual valve 52, and the second valve 53 has been described as being operated under the control of the microprocessor 50, in some embodiments of the invention, it is envisaged that the second valve 53 may be omitted, and control of exhaust gases from the cavity during purging would be appropriately controlled by manually operating the manual valve 52. Needless to say, exhausting of the gases from the cavity may be by any other suitable means instead of the exhaust valves 52 and 53, for example, the cavity could be exhausted through an exhaust valve in the second trocar.

It is also envisaged that the diverter valve 77 which has been described with reference to the leak detecting apparatus 75 for diverting the insufflating gas from the external insufflator 76 into the balloon 78 during operation of the apparatus 75 in the first and second modes, may, instead of being provided by a solenoid operated valve under the control of the microcontroller 50 of the apparatus 75, be provided as a manually operated diverter valve, and would be manually operated at the appropriate time.

While the reservoir 78 in the embodiment of the apparatus described with reference to FIG. 3 has been described as comprising a balloon, any other suitable reservoir or container could be used. Indeed, it is envisaged that the reservoir may be a solid non-expanding and non-yielding structure. It is also envisaged that in the case of the embodiment of the apparatus described with reference to FIG. 3, the reservoir may be omitted, and in which case, the external insufflator 76 would be deactivated during operation of the apparatus 75 when operating in either the first mode or the second mode, in order to avoid the external insufflator activating its alarm.

While specific pressures of the gases in the cavity and in the hollow organ or structure on which the procedure is being carried out, have been described during operation of the leak detecting apparatus in the first and second modes, it is envisaged that the pressures in the cavity and in the hollow structure may be different than those described. Indeed, it is envisaged that when the apparatus are operating as described with reference to FIGS. 1 to 4, the predefined pressure value during operation of the apparatus in either the first or the second mode in the cavity may be as low as 3 mmHg, and may be as high as 15 mmHg, although it is preferable that the predefined pressure value should be in the range of 4 mmHg to 12 mmHg, and ideally, in the range of 5 mmHg to 10 mmHg. When the apparatus of FIGS. 1, 2 and 4 are operating whereby the cavity is being insufflated with the first gas by the first insufflator, and the hollow organ or structure is being insufflated with the second gas by the second or external insufflator, it is envisaged that the predefined pressure value during operation of the apparatus in either the first or second mode in the hollow organ or structure may be as low as 3 mmHg, and may be as high as 15 mmHg, although it is preferable that the predefined pressure value should lie in the range of 4 mmHg to 12 mmHg, and ideally, in the range of 5 mmHg to 10 mmHg.

It will also be appreciated that the constant predefined pressure differential value between the pressure in the hollow structure and the pressure in the cavity may be any other desired valve besides 7 mmHg. Indeed, it will be appreciated that the constant predefined pressure differential valve may lie in the range of 3 mmHg to 15 mmHg, although it is preferable that the constant predefined pressure differential value may lie in the range of 3 mmHg to 12 mmHg, and advantageously, at a constant pressure differential value in the range of 5 mmHg to 10 mmHg, and ideally, at a constant pressure differential value in the order of 7 mmHg or 8 mmHg.

When the apparatus is operating in the first mode, the computation of the size of the leak has been described as being determined as a function of the concentration of the first gas in the exhaust gases exhausted from the cavity at the end of a predefined time period from the commencement of delivery of the first gas to the hollow structure, and also as a function of the change in the concentration of the first gas in the exhaust gases exhausted from the cavity during a predefined time period, it will be readily apparent to those skilled in the art that the size of the leak may be computed as a function of any parameter of the detected first gas in the exhaust gases, for example, the size of the leak in the hollow structure may be computed as any function which describes the temporal variation of the concentration of the first gas during the predefined time period, and may be determined as a function of the integral of concentration of the samples of the first gas in the exhaust gases exhausted from the cavity with respect to time during the predefined time period, or a part thereof. The size of the leak may also be computed as a function of the variation of the concentration of the first gas in the exhaust gases exhausted from the cavity at the end of a predefined period or at any time or at various ones of the predefined sampling time intervals during the predefined time period. Additionally, it is envisaged that the size of the leak from the hollow structure may be determined as a function of the rate of change of the concentration of the first gas at any time during the predefined time period, at the end of the predefined time period or at a number of the predefined sampling time intervals during a predefined time period. It is also envisaged that the size of the leak could be determined as a function of the time for the concentration of the first gas in the exhaust gases to reach a predefined threshold concentration.

It is also envisaged that the size of the leak through a sutured site or an otherwise repaired site in a hollow structure into a cavity in a human or animal body or from any other perforation in a hollow structure into a cavity in a human or animal body may be computed as a function of either the average flow rate of the first gas delivered into the hollow structure or cavity as the case may be during the predefined period or a selected part thereof, or the average concentration of the first gas in the gases exhausted from the cavity or the hollow structure as the case may be during the predefined time period or a selected part thereof.

It is also envisaged that the passive one-way valve 46 may be replaced by a solenoid operated normally open valve which would be located adjacent the exhaust port 40 and which would operate under the control of the microprocessor 50. However, if the passive one-way valve 46 were being replaced by such a solenoid operated valve, a pressure sensor would be required in the communicating conduit 35 adjacent such a solenoid valve on the upstream side thereof for monitoring the pressure in the communicating conduit 35 downstream of the T-connector 38 and adjacent the solenoid valve. In which case, the microprocessor 50 would be configured to read signals from the pressure sensor, and would be responsive to the signals from the pressure sensor being indicative of the pressure adjacent the solenoid valve falling below a predefined threshold value for operating the solenoid valve from the normally open state to a closed state, in order to avoid the exhaust gases being sampled by the gas detector 18 containing air, that would otherwise be drawn into the gas detector 18 through the exhaust port 40, in the event of the flow rate of the exhaust gases from the cavity 7 or 65 falling below the sampling rate of 200 ml per minute of the gas detector. The solenoid 30) valve would be retained by the microprocessor 50 in the closed state until the pressure monitored by the pressure sensor transitioned above the predefined threshold pressure.

While the pressure sensors for monitoring the pressure in the hollow organ and in the cavity have been described as being remotely located in the various apparatus, it is envisaged that in some embodiments of the invention one or both of the pressure sensors for monitoring the pressure in the hollow organ and/or in the cavity may be physically located in or adjacent the hollow organ 3 and/or the cavity, and the pressure sensors would then communicate with the microprocessor 50 of the apparatus either by hard wiring or by wireless communication.

While the flow meter 25 has been described as being a standalone flow meter, it is envisaged that the flow meter 25 may be integrated as a component of the first pressure regulator 21.

While the predefined pressure value and the predefined pressure differential value have been described as being selectable, while this is advantageous, it is not essential, and in some cases only one of the predefined pressure value and the predefined pressure differential value may be selectable, and in other cases, neither of the predefined pressure value or the predefined pressure differential value would be selectable.

It is also envisaged that while the predefined time period and the predefined sampling time intervals have been described as being selectable, in some embodiments of the invention it is envisaged that neither the predefined time period nor the predefined sampling time intervals would be selectable, and in other embodiments of the invention only one of the predefined time period and the predefined sampling time intervals would be selectable.

Where the apparatus are configured as described with reference to FIGS. 1 to 4, and are being used for detecting and determining the size of a leak through a sutured or otherwise repaired site in, for example, an intestine, in particular, the small intestine, it is envisaged that the first delivery conduit and the first static pressure conduit, if such was provided could be entered into the intestine transorally or transnasally. Additionally, where the apparatus is configured as described with reference to FIGS. 1 to 4, and is being used to detect and determine the size of a leak in the rectum, colon or the large intestine, it is envisaged that the first delivery conduit, the first static pressure conduit if such is provided could be entered into the rectum, the colon or the large intestine through the anus.

It is also envisaged that in embodiments of the invention where the apparatus are being operated whereby the cavity is being insufflated with the first gas by the first insufflator and the hollow organ or structure is being insufflated with the second gas by the second insufflator, if the hollow organ is either the stomach or the small intestine, it is envisaged that the second delivery tube, the second static pressure tube, if such is provided and the communicating conduit 35 would be entered into the stomach or the small intestine transorally or transnasally, and in such a case where the hollow organ is the rectum, the colon or the large intestine, the second delivery conduit, the second static pressure conduit, if such is provided and the communicating conduit 35 would be entered into the rectum, the colon or the large intestine through the anus.

Needless to say, the hollow organ may be any other organ besides an organ in the digestive track, and in which case, suitable access would be provided to the hollow organ for the first delivery conduit and the first static pressure conduit if such is provided, in the case where the apparatus is being operated in the first or second mode as described with reference to FIGS. 1 to 4, or for the second delivery conduit, the second static pressure conduit if such is provided and the communicating conduit where the apparatus is being operated with the cavity being insufflated with the first gas by the first insufflator and the hollow organ or structure being insufflated with the second gas by the second insufflator.

When the leak detecting apparatus is being used in the configuration described with reference to FIGS. 1 to 4 to detect and to determine the size of a leak from a hollow organ, which is not accessible through a body orifice, it is envisaged that access to the hollow organ for accommodating the first gas thereto may be provided from the cavity, whereby a small gauge needle would be provided to deliver the first gas into the hollow organ. On the other hand, when the hollow organ is not accessible through a body orifice, and the apparatus is being operated in the configuration where the second gas is delivered to the hollow organ, and the gases are exhausted from the hollow organ, it is envisaged that access to the hollow organ for delivery of the second gas thereto and for exhausting of the gases therefrom would be provided from the cavity through two small gauge needles into the hollow organ.

It will also be appreciated that the leak detecting apparatus may be provided without a second insufflator and without an external insufflator. In which case, when the apparatus is being operated in the configuration described with reference to FIGS. 1 to 4, the first gas would be delivered to the hollow organ by the first insufflator, and any gases in the cavity would be exhausted, and the gas detector would sample the gases exhausted from the cavity to detect the first gas in the gases exhausted from the cavity.

On the other hand, when the apparatus is being operated in the configuration whereby the first gas is delivered into the cavity, it will be appreciated that the leak detecting apparatus may be provided without a second insufflator and without an external insufflator, and in which case, the apparatus and method would be used to only deliver the first gas into the cavity, and the gases in the hollow organ would be exhausted therefrom, and the gas detector would sample the gases exhausted from the hollow organ for detecting the first gas.

Inserting a small gauge needle or small gauge needles into the hollow organ should not in any way damage the hollow organ, and on removal of the small gauge needle or needles, the natural healing ability of the body will rapidly reseal the hollow organ after removal of the small gauge needle or needles.

While the apparatus and method have been described for detecting and determining the size of a leak in a sutured, repaired or perforated site in a hollow organ, which may be the result of closing an opening in the hollow organ formed during a surgical procedure, it is envisaged that the apparatus and method may be used for detecting and determining the size of any perforation from any hollow organ into a cavity in a human or animal body which may have resulted from a disease or other causes.

The invention claimed is:

1. A leak detecting apparatus for detecting a leak in a hollow structure located in a cavity in a human or animal body, the leak detection apparatus comprising:
  a first insufflator configured to deliver a first gas into one of the hollow structure or the cavity,
  a first pressure sensor configured to produce a signal indicative of a pressure in the hollow structure,
  a second pressure sensor configured to produce a signal indicative of a pressure in the cavity,
  a pressure regulator in communication with a processor, the pressure regulator configured to control the pressure in one of the hollow structure or the cavity for maintaining a substantially constant pressure differential between the pressure in the hollow structure and the pressure in the cavity, one of
    a gas detector configured to produce a signal indicative of a presence of the first gas in the hollow structure or the cavity into which the first gas is not delivered, or
    a flow meter configured to produce a signal indicative of a rate of flow of the first gas delivered to the one of the hollow structure or the cavity,
  the processor configured to compute a size of the leak as a function of the pressure differential between the pressure in the hollow structure and the pressure in the cavity, and at least one of
    the presence of the first gas in the hollow structure or the cavity into which the first gas is not delivered, or
    the rate of flow of the first gas to the one of the hollow structure or the cavity.

2. The leak detecting apparatus of claim 1 wherein the pressure regulator and the processor are configured to control the pressure in the one of the hollow structure or the cavity, so that the pressure in the one of the hollow structure or the cavity into which the first gas is delivered, is at a higher pressure than the pressure in the hollow structure or the cavity into which the first gas is not delivered.

3. The leak detecting apparatus of claim 1 wherein the first insufflator is configured to operate under control of the processor.

4. The leak detecting apparatus of claim 1, wherein the processor is configured to compute the size of the leak from the signals produced by the first pressure sensor and the second pressure sensor.

5. The leak detecting apparatus of claim 1, further including a second insufflator, the second insufflator being configured to insufflate the hollow structure or the cavity, into which the first gas is not delivered, with a second gas.

6. The leak detecting apparatus of claim 5, wherein the second insufflator is configured to operate under control of the pressure regulator to control the pressure in the hollow structure or the cavity, into which the second gas is delivered.

7. The leak detecting apparatus of claim 5, wherein the first gas is the same as the second gas or different from the second gas.

8. The leak detecting apparatus of claim 5, wherein the second insufflator is an external insufflator couplable with the leak detecting apparatus, the leak detecting apparatus configured to operate in conjunction with the external insufflator when they are coupled.

9. The leak detecting apparatus of claim 8 further including a diverting valve, the diverting valve being selectively and alternately operable in a normal state for delivering the second gas from the external insufflator to the hollow structure or the cavity, and in a diverting state for delivering the second gas from the external insufflator to a reservoir, the reservoir being configured for maintaining a pressure of the second gas delivered by the external insufflator at a pressure value corresponding to a normal operating pressure value at which the external insufflator is configured to operate.

10. The leak detecting apparatus of claim 1 wherein the first gas comprises one of a gas not naturally occurring in the hollow organ or the cavity of the human or animal body, or a gas which occurs naturally in the hollow organ or the cavity of the human or animal body in negligible amounts.

11. A leak detecting apparatus for detecting a leak from a hollow structure in a human or animal body to a cavity in the human or animal body, the leak detection apparatus comprising:
  a first insufflator configured to deliver a first gas into the hollow structure, a first pressure sensor configured to produce a signal indicative of a pressure in the hollow structure, a second pressure sensor configured to produce a signal indicative of a pressure in the cavity, a pressure regulator in communication with a processor, the pressure regulator configured to control the pressure in one of the hollow structure or the cavity for maintaining a substantially constant pressure differential between the pressure in the hollow structure and the pressure in the cavity, one of a gas detector configured to produce a signal indicative of a presence of the first gas in the cavity, or a flow meter configured to produce a signal indicative of a rate of flow of the first gas delivered to the hollow structure, and the processor configured to compute a size of the leak as a function of the pressure differential between the pressure in the hollow structure and the pressure in the cavity, and at least one of the presence of the first gas in the cavity, or the rate of flow of the first gas to the hollow structure.

12. A method for detecting a leak in a hollow structure located in a cavity in a human or an animal body, the method comprising:

delivering a first gas into one of the hollow structure or the cavity, monitoring a pressure in the hollow structure, monitoring a pressure in the cavity, controlling the pressure in one of the hollow structure or the cavity for maintaining a substantially constant pressure differential between the pressure in the hollow structure and the pressure in the cavity by controlling the delivery of the first gas to the one of the hollow structure or the cavity, monitoring a rate of flow of the first gas being delivered to the one of the hollow structure or the cavity while the pressure differential between the pressure in the hollow structure and the pressure in the cavity is being maintained substantially constant, and computing a size of the leak as a function of the pressure differential between the pressure in the hollow structure and the pressure in the cavity, and the monitored rate of flow of the first gas to the one of the hollow structure or the cavity while the pressure differential between the pressure in the hollow structure and the pressure in the cavity is being maintained substantially constant.

13. The method as claimed in claim 12 further comprising controlling one of the pressure in the hollow structure or the pressure in the cavity, so that the pressure in the one of the hollow structure or the cavity into which the first gas is delivered, is at a higher pressure than the pressure in another one of the hollow structure or the cavity.

14. The method of claim 12 further comprising controlling the pressure in the one of the hollow structure or the cavity, into which the first gas is delivered relative to the pressure in another one of the hollow structure or the cavity.

15. The method of claim 12 further comprising delivering a second gas into another one of the hollow structure or the cavity, into which the first gas is not delivered.

16. The method of claim 15 wherein the pressure in the another one of the hollow structure or the cavity, into which the second gas is delivered, is maintained at a predefined pressure value.

17. The method as claimed in claim 16 wherein the predefined pressure value lies in a range of 5 mmHg to 10 mmHg.

18. The method as claimed in claim 15 wherein the first gas is the same as the second gas.

19. The method as claimed in claim 15 wherein the delivering the second gas comprises delivering the second gas into the cavity.

20. The method as claimed in claim 12 wherein the pressure in the one of the hollow structure or the cavity is controlled relative to the pressure in another one of the hollow structure or the cavity.

21. The method of claim 12 further comprising controlling one of the pressure in the hollow structure or the cavity for maintaining the pressure differential between the pressure in the hollow structure and the pressure in the cavity substantially constant at a predefined pressure differential value.

22. The method as claimed in claim 21 wherein the predefined pressure differential value lies in a range of 3 mmHg to 12 mmHg.

23. The method as claimed in claim 21 wherein the predefined pressure differential value is selectable.

24. The method of claim 12 wherein the delivering the first gas comprises delivering the first gas into the hollow structure.

25. A method for detecting a leak from a hollow structure in a human or animal body to a cavity in the human or animal body, the method comprising:

delivering a first gas into the hollow structure, monitoring a pressure in the hollow structure, monitoring a pressure in the cavity, controlling the pressure in one of the hollow structure or the cavity for maintaining a substantially constant pressure differential between the pressure in the hollow structure and the pressure in the cavity, monitoring one of: gas in the cavity or gas exhausted from the cavity for a presence of the first gas, or a rate of flow of the first gas delivered to the hollow structure, and computing a size of the leak as a function of the pressure differential between the pressure in the hollow structure and the pressure in the cavity, and one of the presence of the first gas in the cavity, or the rate of flow of the first gas to the hollow structure.

26. A method for detecting a leak in a hollow structure located in a cavity in a human or an animal body, the method comprising:

delivering a first gas into one of the hollow structure or the cavity, monitoring a pressure in the hollow structure, monitoring a pressure in the cavity, controlling the pressure in one of the hollow structure or the cavity for maintaining a substantially constant pressure differential between the pressure in the hollow structure and the pressure in the cavity by controlling the delivery of the first gas to the one of the hollow structure or the cavity, monitoring a rate of flow of the first gas being delivered to the one of the hollow structure or the cavity while the pressure differential between the pressure in the hollow structure and the pressure in the cavity is being maintained substantially constant, and computing a size of the leak as a function of the monitored rate of flow of the first gas to the one of the hollow structure or the cavity while the pressure differential between the pressure in the hollow structure and the pressure in the cavity is being maintained substantially constant.

27. The method as claimed in claim 26 further comprising controlling one of the pressure in the hollow structure or the pressure in the cavity, so that the pressure in the one of the hollow structure or the cavity into which the first gas is delivered, is at a higher pressure than the pressure in the other one of the hollow structure or the cavity.

28. The method as claimed in claim 26 further comprising controlling the pressure in the one of the hollow structure or the cavity, into which the first gas is delivered for maintaining the pressure differential between the pressure in the hollow structure and the pressure in the cavity substantially constant at a predefined pressure differential value.

29. The method as claimed in claim 26 further comprising delivering a second gas into the hollow structure or the cavity, into which the first gas is not delivered.

30. The method as claimed in claim 29 wherein the pressure in the hollow structure or the cavity, into which the second gas is delivered, is maintained at a predefined pressure value.

31. The method as claimed in claim 29 wherein the first gas is the same as the second gas.

32. The method as claimed in claim 29 wherein the delivering the second gas comprises delivering the second gas into the cavity.

\* \* \* \* \*